(12) United States Patent
Yoon et al.

(10) Patent No.: US 11,389,516 B2
(45) Date of Patent: Jul. 19, 2022

(54) COMPOSITION COMPRISING UNE-L DOMAIN OF LEUCYL-TRNA SYNTHETASE AS EFFECTIVE INGREDIENT FOR AUGMENTING MUSCLE

(71) Applicants: GACHON UNIVERSITY OF INDUSTRY-ACADEMIC COOPERATION FOUNDATION, Gyeonggi-do (KR); GIL MEDICAL CENTER, Incheon (KR)

(72) Inventors: Mee Sup Yoon, Incheon (KR); Jie Chen, Urbana, IL (US); Kook Son, Busan (KR); Cheol Soo Choi, Incheon (KR); Sunghoon Kim, Seoul (KR); Jung Min Han, Gwangju (KR)

(73) Assignees: Gachon University of Industry-Academic Cooperation Foundation, Gyeonggi-Do (KR); Gil Medical Center, Incheon (KR)

( * ) Notice: Subject to any disclaimer, the term of this patent is extended or adjusted under 35 U.S.C. 154(b) by 438 days.

(21) Appl. No.: 16/678,369

(22) Filed: Nov. 8, 2019

(65) Prior Publication Data

US 2020/0155655 A1 May 21, 2020

Related U.S. Application Data

(63) Continuation-in-part of application No. PCT/KR2018/005311, filed on May 9, 2018.

(30) Foreign Application Priority Data

May 9, 2017 (KR) .......... 10-2017-0057777
Sep. 28, 2017 (KR) .......... 10-2017-0126082

(51) Int. Cl.
*A61K 38/53* (2006.01)
*A61P 21/06* (2006.01)
*C12N 9/00* (2006.01)
*G01N 33/50* (2006.01)

(52) U.S. Cl.
CPC .......... *A61K 38/53* (2013.01); *A61P 21/06* (2018.01); *C12N 9/93* (2013.01); *C12Y 601/01004* (2013.01); *G01N 33/5023* (2013.01)

(58) Field of Classification Search
None
See application file for complete search history.

(56) References Cited

FOREIGN PATENT DOCUMENTS

KR 20170032652 3/2017
WO 201114641 A2 11/2011

OTHER PUBLICATIONS

Crozier SJ et al., J Nutr. 135:376-382, 2005.
Stipanuk MH, "Leucine and Protein Synthesis: mTOR and Beyond", Journal Article, Mar. 2007, Nutrition Reviews, 65, pp. 122-129, Oxford University Press, UK.
Yoon, et al., "Class III PI-3-Kinase Activates Phospholipase D in an Amino Acid-Sensing mTORC1 Pathway", Journal Article, 2011, J Cell Biol., 195(3), pp. 435-447, The Rockerfeller University Press, USA.
Sun, et al., "Phospholipase D1 is an Effector of Rheb in the mTOR Pathway", 2008, Journal Article, 105(24), pp. 8286-8291, The National Academy of Sciences of the USA, USA.
Yan, et al., "hVps15, but not Ca2+/CaM, is Required for the Activity and Regulation of hVps34 in Mammalian Cells", Journal Aritcle, 2009, Biochem J., 417(3), pp. 747-755, The Authors Journal Compilation, UK.
Han, et al., "Leucyl-tRNA Sythetase is an Intracellular Leucine Sensor for the mTORCI-Signaling Pathway", Journal Article, 2012, Cell 149(2), pp. 410-424, Elsevier Inc., Netherlands.
Han, et al., "Hierarchical Network Between the Components of the Multi-tRNA Synthetase Complex, Implications for Complex Formation", Journal Article, 2006, J Biol Chem., 281(50), pp. 38663-38667, The Journal of Biological Chemistry, USA.
Yuan, et al., "Regulation of PIK3C3/VPS34 complexes by MTOR in nutrient stress-induced autophagy", Journal Article, 2013, Autophagy, 9(12), pp. 1983-1995, Landes Biosciense, USA.
Fang, et al., "PLD1 Regulates mTOR Signaling and Mediates Cdc42 Activation of S6K1", Journal Article, 2003, Curr Biol., 13(23), pp. 2037-2044, Elsevier Science, Ltd. Netherlands.
Agard et al., "Flourescence Microscopy in Three Dimensions", book, 1989, pp. 354-378, John Innes Institure, UK.
Yoon et al., "Distinct amino acid-sensing mTOR pathways regulate skeletal myogenesis", Journal Article, 2013, Amino acid signaling in myogenesis, 24(23), pp. 3754-3763, Molecular biology of the cell, USA.
Sun et al., "IGF-II is regulated by microRNA-125b in skeletal myogenesis", Journal Article, 2011, J. Cell Biol. 192, pp. 69-81, The Rockerfeller University Press, USA.
Yoon et al., "Leucyl-tRNA Synthetase Activates Vps34 in Amino Acid-Sensing mTORCI Signaling", Journal Article, 2016, Cell Reports, 16, pp. 1510-1517, Open Access Cell Press, USA.
Suryawan et al., "Regulation of Leucine-induced mTORCI Activation in Skeletal Muscle of Neonatal Pigs", Journal Article, 2017, The FASEB Journal, 31, Federation of American Societies for Experimental Biology, USA.

(Continued)

*Primary Examiner* — Kagnew H Gebreyesus

(57) ABSTRACT

The present invention relates to a composition comprising the UNE-L domain of leucyl-tRNA synthetase as an effective ingredient for increasing muscle. More particularly, the UNE-L domain of LRS according to the present invention, which is a region that controls activity of Vps34, activates mTORC1 involved in protein synthesis and increases myocyte differentiation and muscle fiber regeneration, thus finding useful application in muscle augmentation.

6 Claims, 17 Drawing Sheets

Specification includes a Sequence Listing.

(56) References Cited

OTHER PUBLICATIONS

GenBank: BC152422.1, *Homo sapiens* leucyl-tRNA synthetase, mRNA (cDNA clone MGC:176655 IMAGE:8862534), complete cds, database, 2018.
GenBank: EAW61850.1, leucyl-tRNA synthetase, isoform CRA c [*Homo sapiens*], database, 2018.
International Search Report issued in PCT/KR2018/005311 dated Feb. 15, 2019.

[Figure 1A]
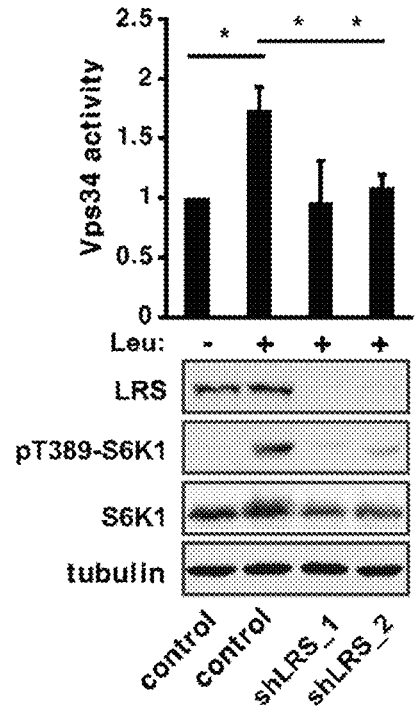
[Figure 1B]
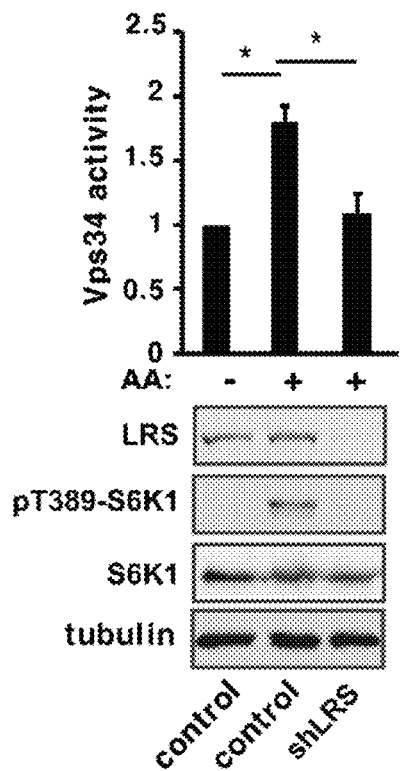

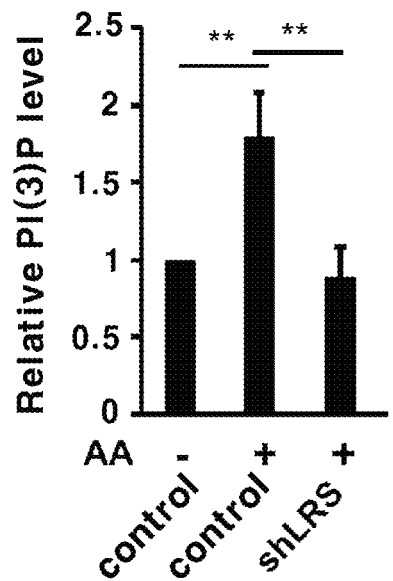
【Figure 1C】
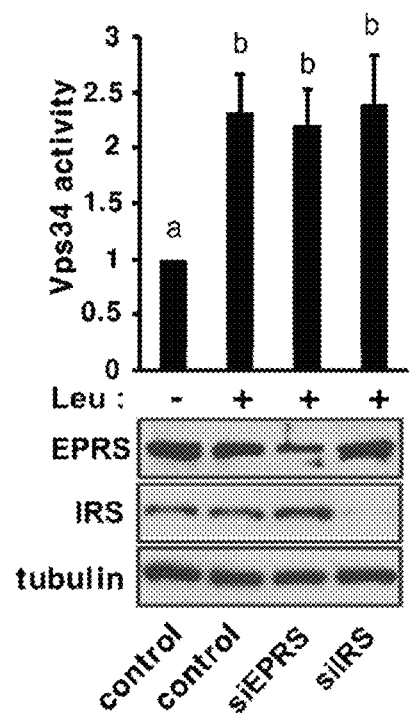
【Figure 2】

[Figure 3A]
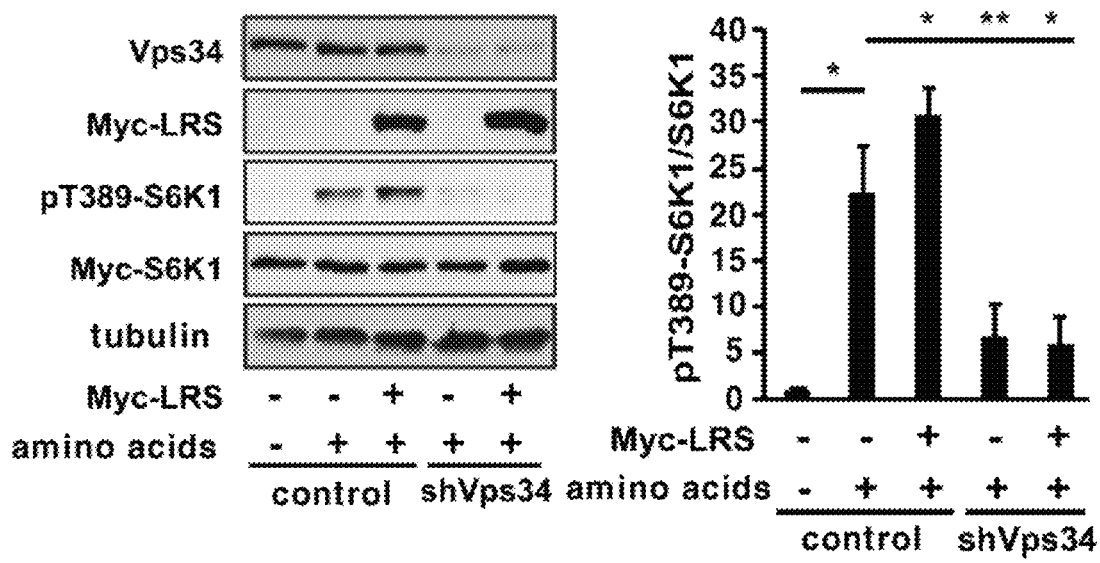
[Figure 3B]
[Figure 3C]
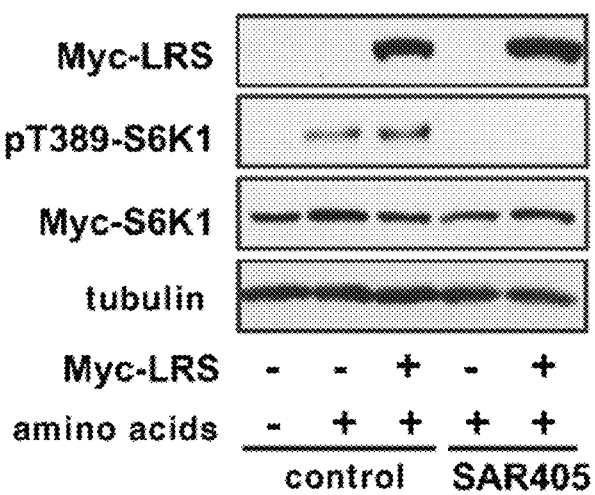

[Figure 4A]
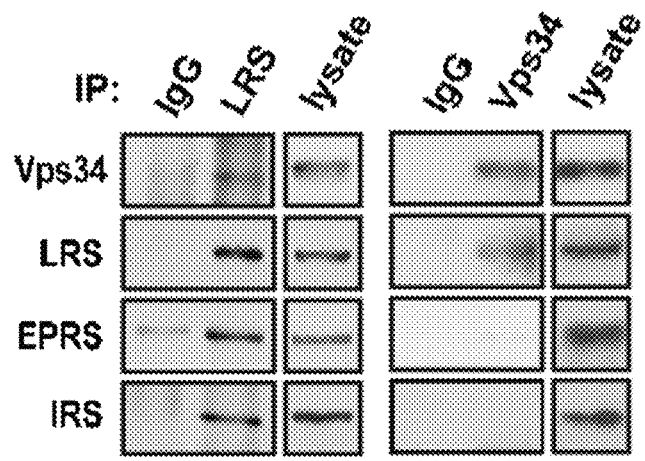
[Figure 4B]
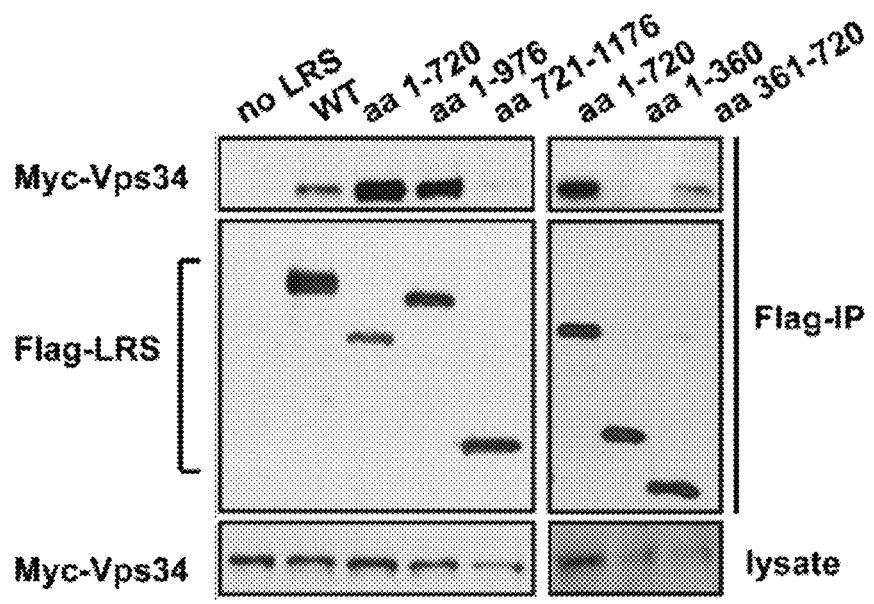

[Figure 4C]
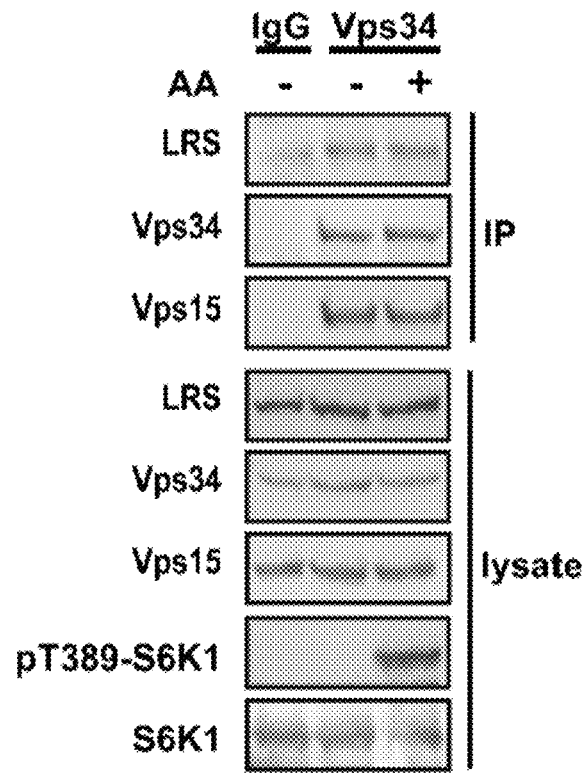
[Figure 4D]
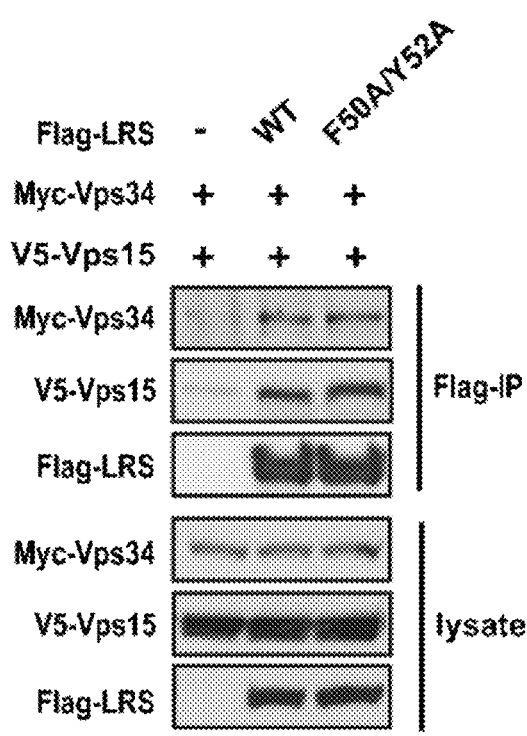

[Figure 5A]
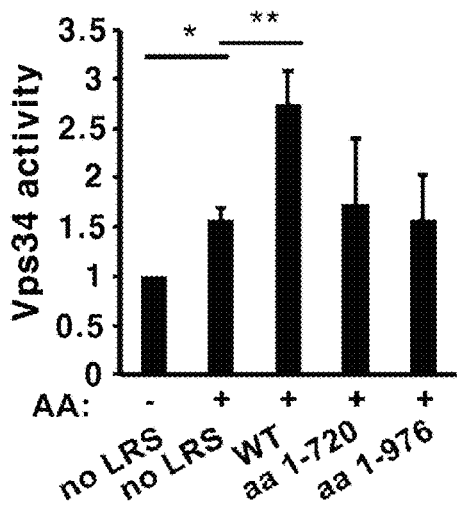
[Figure 5B]
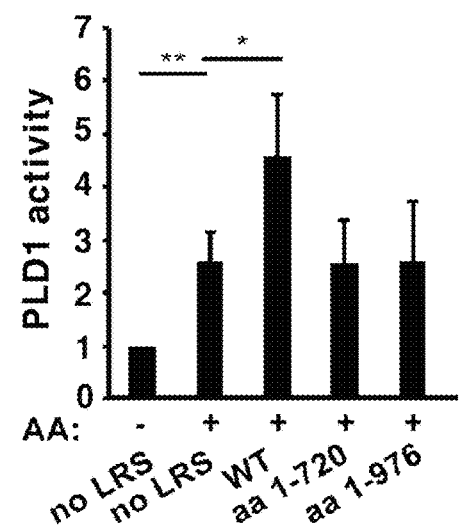
[Figure 5C]
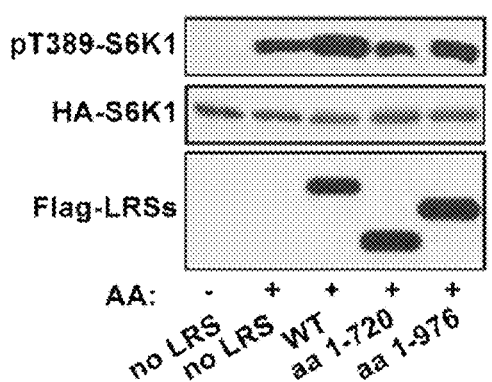

[Figure 5D]
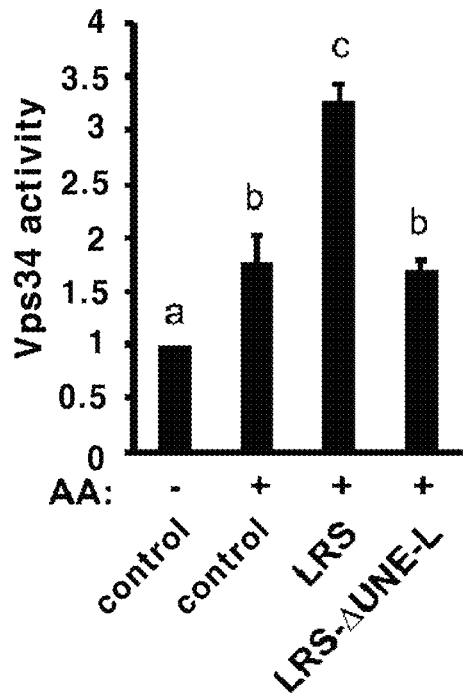
[Figure 5E]
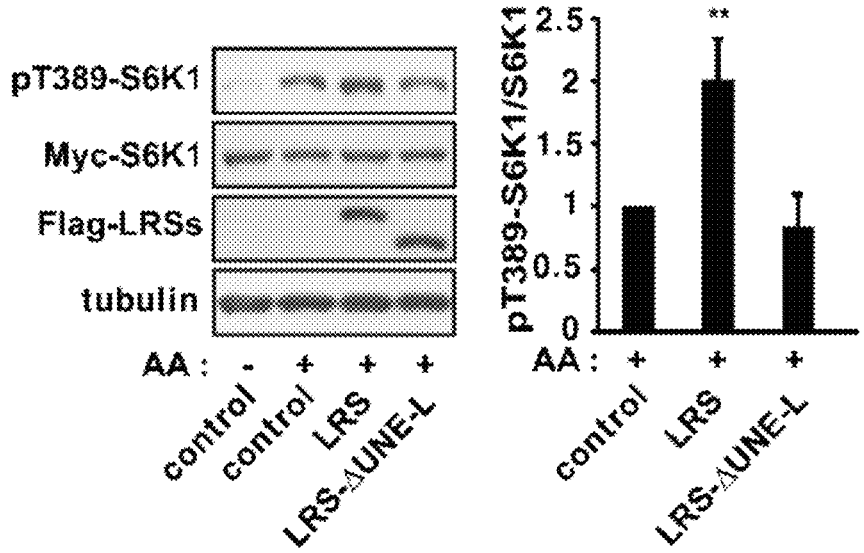

[Figure 6A]
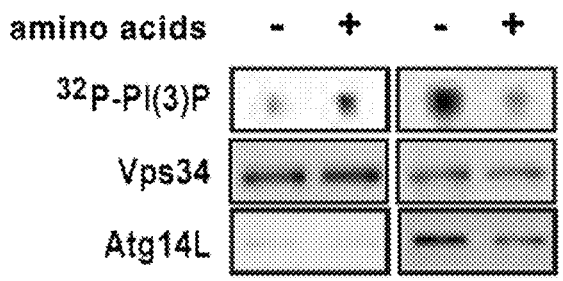
[Figure 6B]
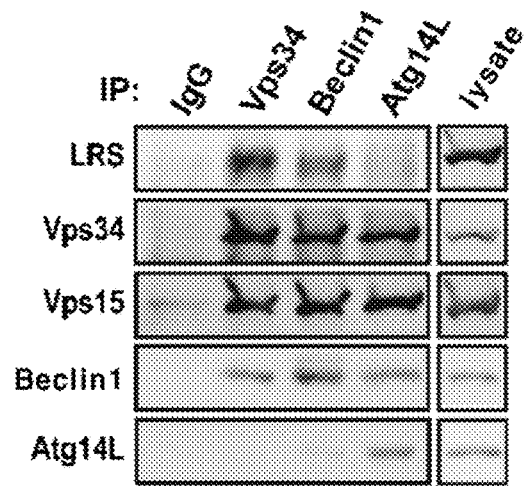
[Figure 7]
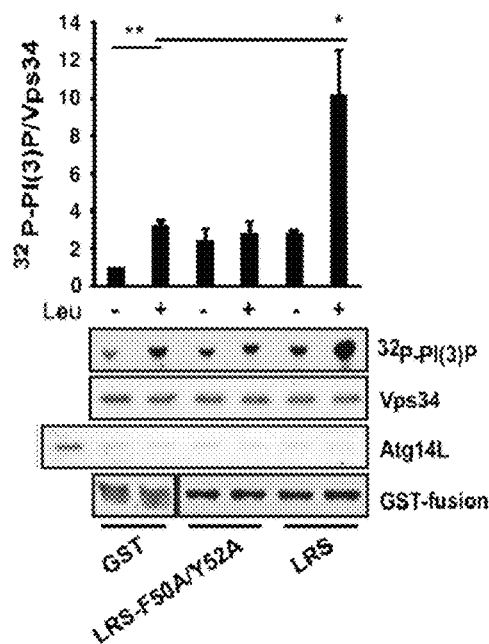

[Figure 8A]
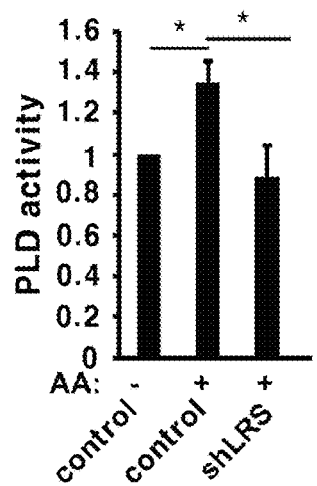
[Figure 8B]
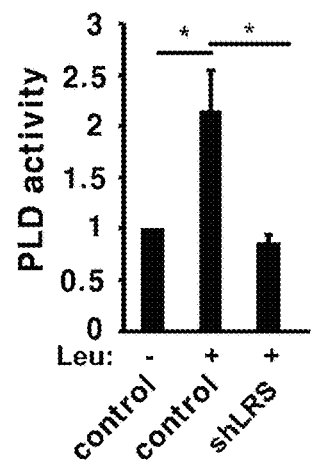
[Figure 9]
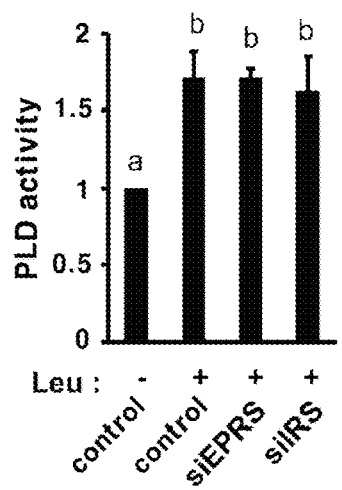

[Figure 10A]
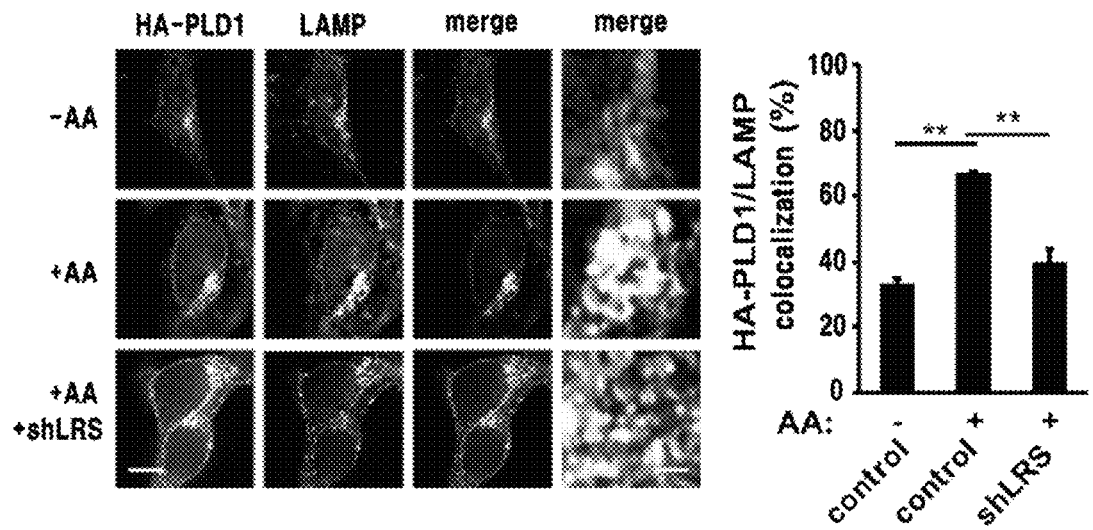
[Figure 10B]
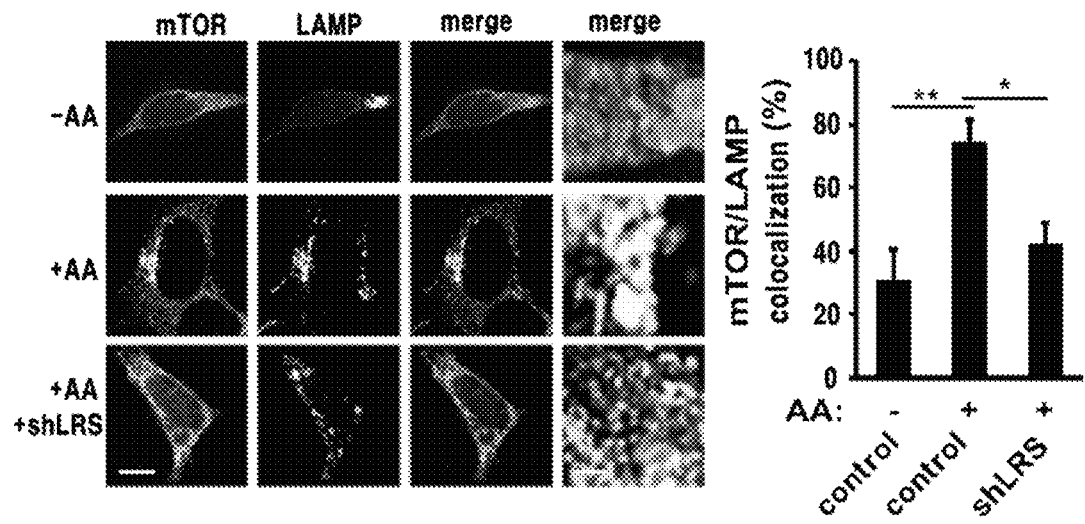

[Figure 11]
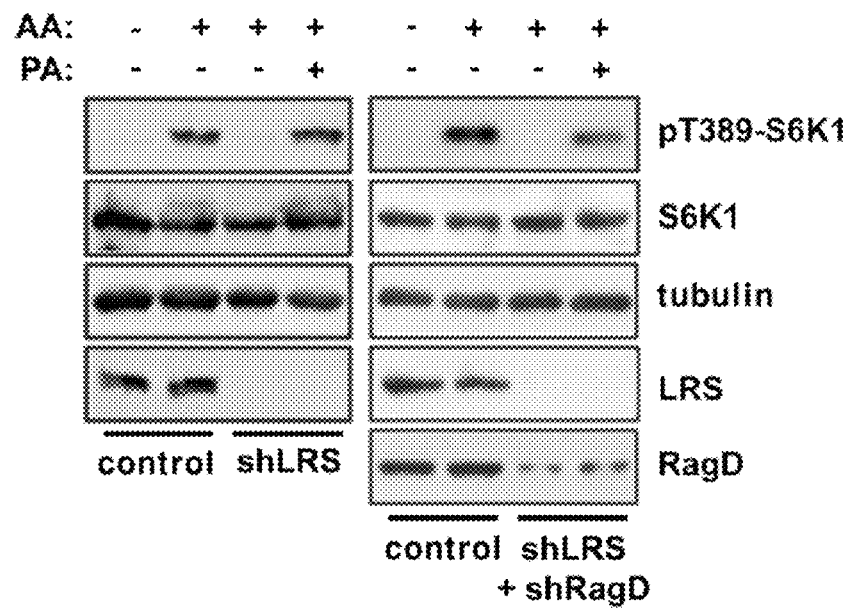
[Figure 12A]
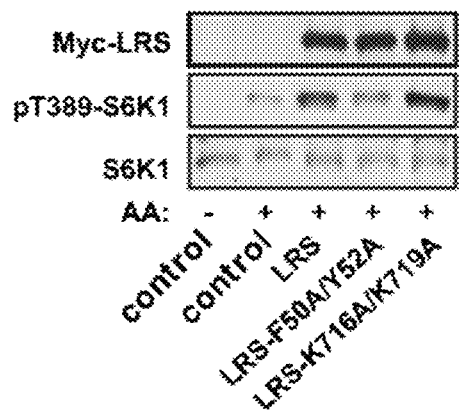

[Figure 12B]
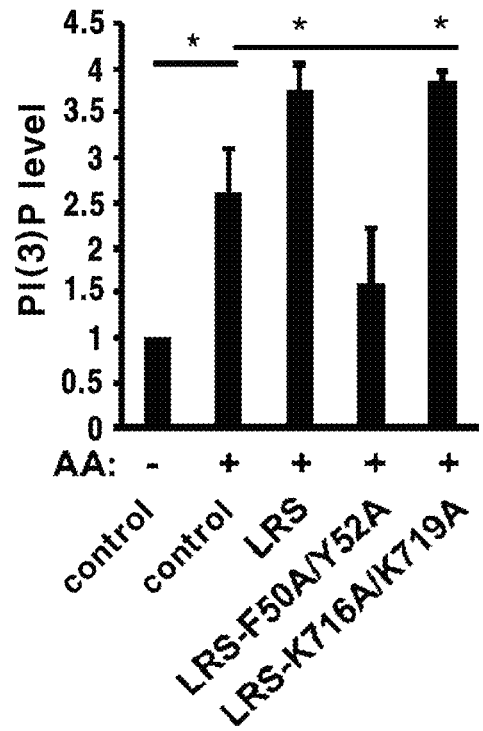
[Figure 12C]
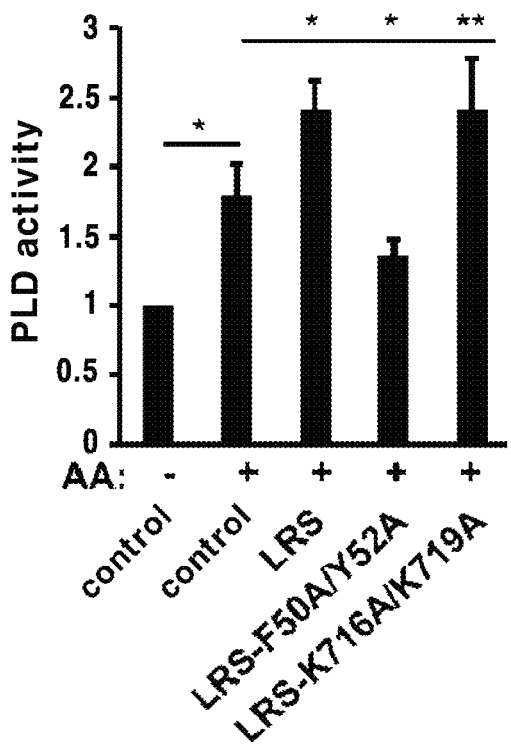

[Figure 13A]
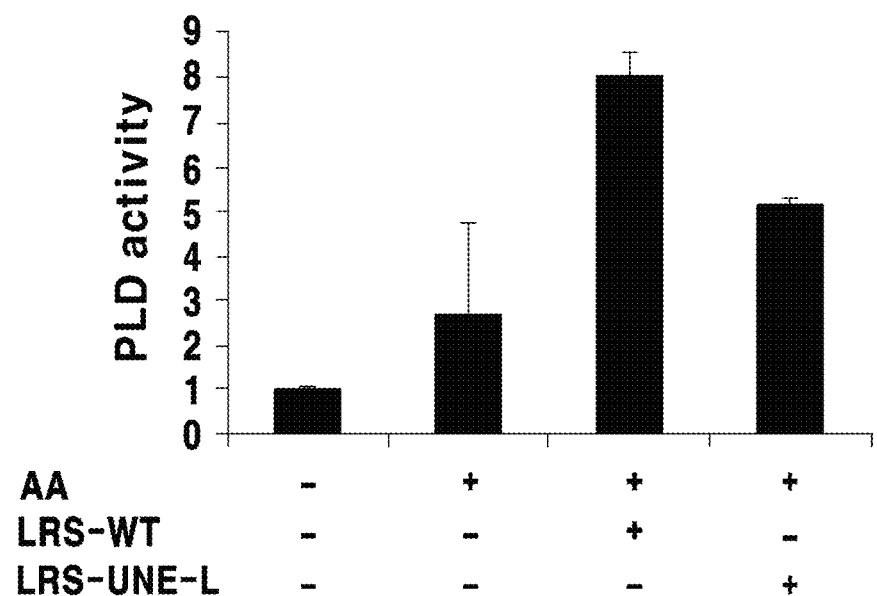
[Figure 13B]
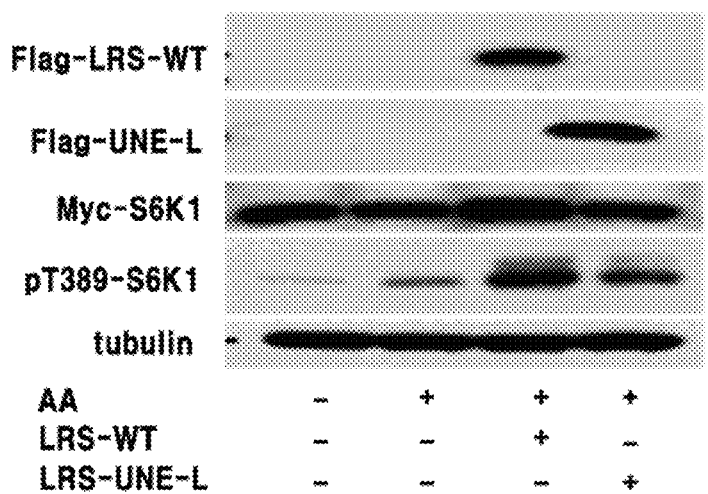

[Figure 14]
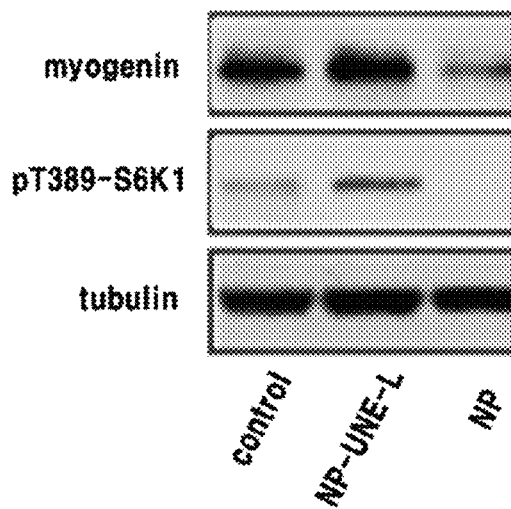
[Figure 15]
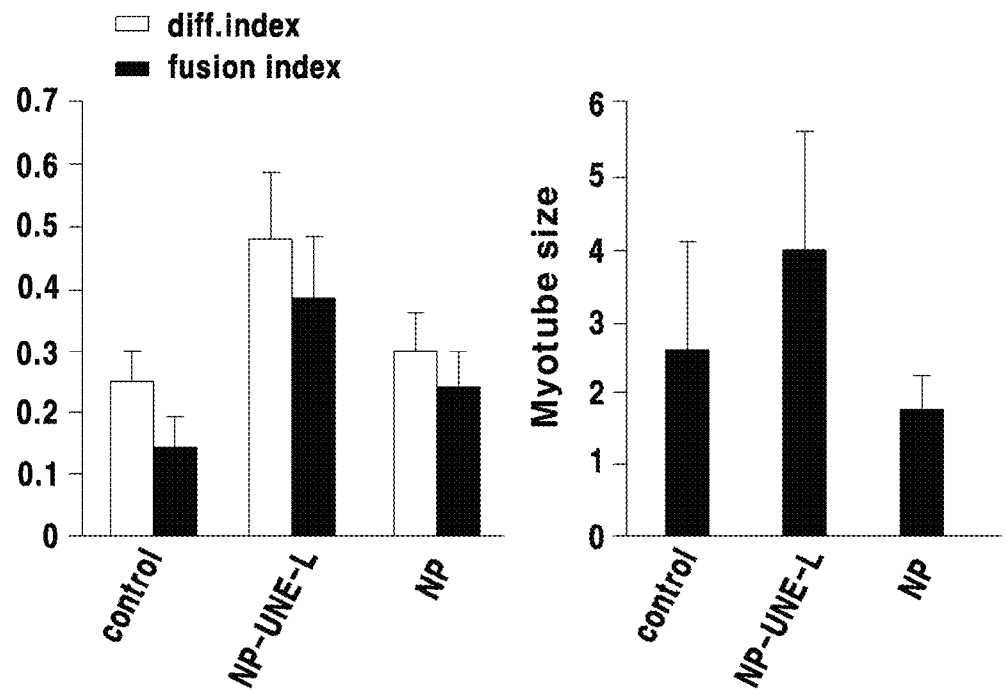

[Figure 16]
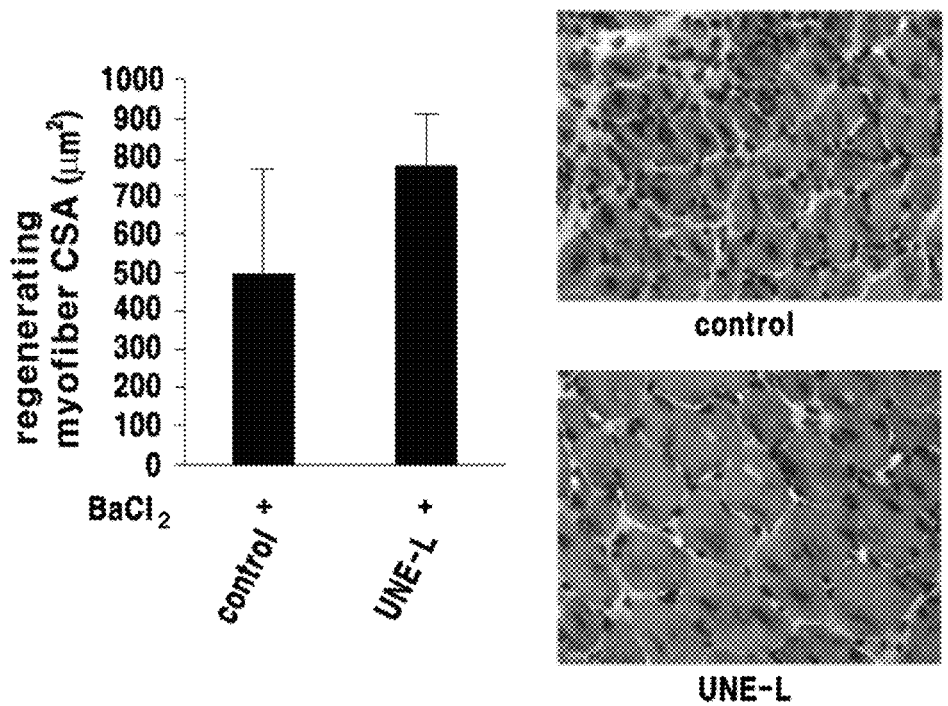
[Figure 17]
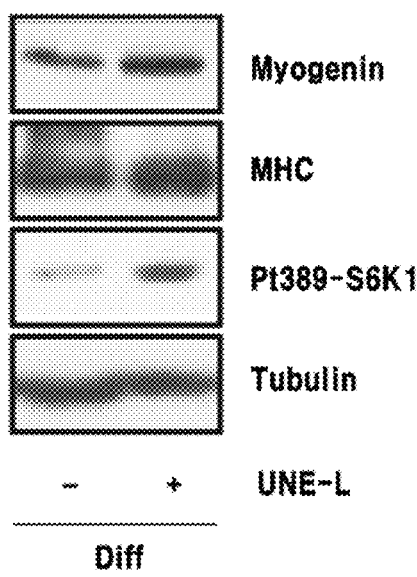

[Figure 18A]
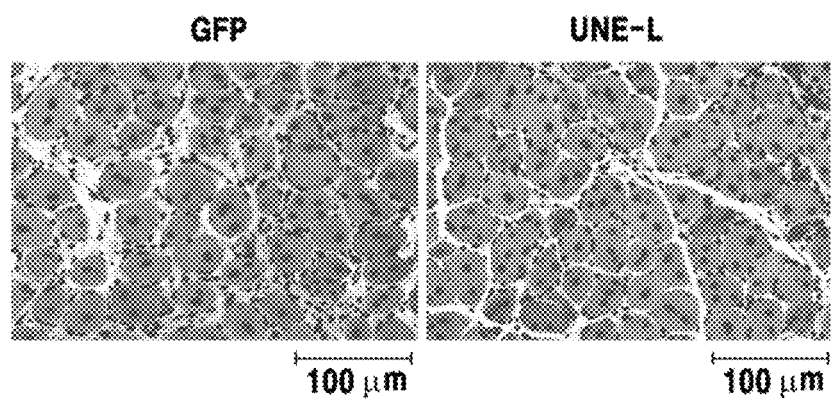
[Figure 18B]
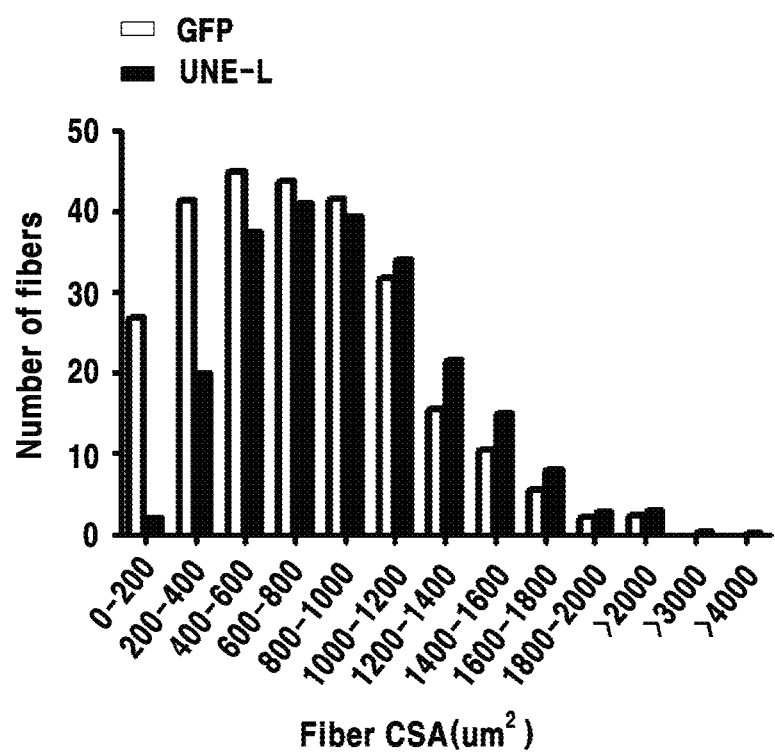

[Figure 18C]
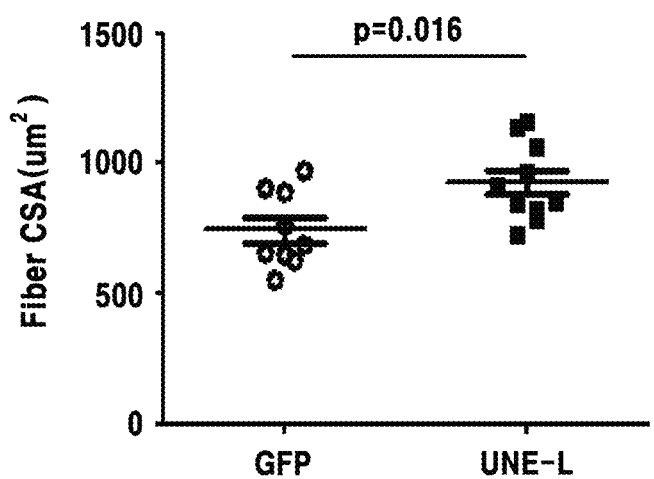
[Figure 19]
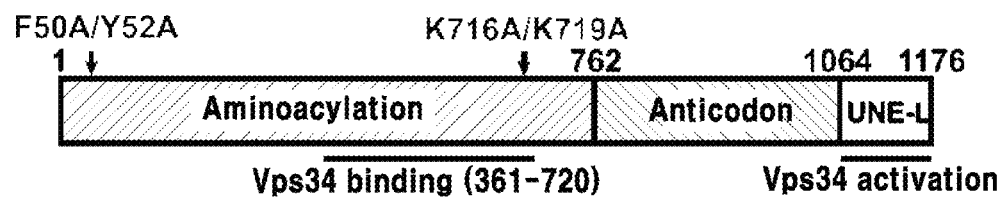

SEQUENCE LISTING

```
<160> NUMBER OF SEQ ID NOS: 2

<210> SEQ ID NO 1
<211> LENGTH: 112
<212> TYPE: PRT
<213> ORGANISM: Homo sapiens

<400> SEQUENCE: 1

Pro Gly Val Ser Val Ser Leu Val Asn Pro Gln Pro Ser Asn Gly His
1               5                   10                  15

Phe Ser Thr Lys Ile Glu Ile Arg Gln Gly Asp Asn Cys Asp Ser Ile
            20                  25                  30

Ile Arg Arg Leu Met Lys Met Asn Arg Gly Ile Lys Asp Leu Ser Lys
        35                  40                  45
```

```
Val Lys Leu Met Arg Phe Asp Asp Pro Leu Leu Gly Pro Arg Arg Val
     50                  55                  60

Pro Val Leu Gly Lys Glu Tyr Thr Glu Lys Thr Pro Ile Ser Glu His
65                   70                  75                  80

Ala Val Phe Asn Val Asp Leu Met Ser Lys Lys Ile His Leu Thr Glu
                 85                  90                  95

Asn Gly Ile Arg Val Asp Ile Gly Asp Thr Ile Ile Tyr Leu Val His
                100                 105                 110

<210> SEQ ID NO 2
<211> LENGTH: 339
<212> TYPE: DNA
<213> ORGANISM: Homo sapiens

<400> SEQUENCE: 2
cctggtgtgt ccgtttctct ggtgaatccc cagccatcca atggccactt ctcaaccaaa      60
attgaaatca ggcaaggaga taactgtgat tccataatca ggcgtttaat gaaaatgaat     120
cgaggaatta aagacctttc caaagtgaaa ctgatgagat ttgatgatcc actgttgggg     180
cctcgacgag ttcctgtcct gggaaaggag tacaccgaga agaccccat ttctgagcat      240 gctgttttca atgtggacct catgagcaag aaaattcatc tgactgagaa tgggataagg     300
gtggatattg gcgatacaat aatctatctg gttcattaa                            339
```

COMPOSITION COMPRISING UNE-L DOMAIN OF LEUCYL-TRNA SYNTHETASE AS EFFECTIVE INGREDIENT FOR AUGMENTING MUSCLE

CROSS-REFERENCE TO RELATED APPLICATIONS

This application is a continuation in part of PCT Application No. PCT/KR2018/005311, filed May 9, 2018, entitled "COMPOSITION COMPRISING UNE-L DOMAIN OF LEUCYL-TRNA SYNTHETASE AS EFFECTIVE INGREDIENT FOR AUGMENTING MUSCLE," which claims benefit of and priority to Korean Patent Application No. 10-2017-0126082, filed Sep. 28, 2017 and Korean Patent Application No. 10-2017-0057777, filed May 9, 2017, all of which are incorporated herein by reference in their entirety.

REFERENCE TO A SEQUENCE LISTING SUBMITTED VIA EFS-WEB

The content of the ASCII text file of the sequence listing named "18931-17_2020-01-22_Sequence-Listing_ST25," which is 2.01 kb in size, was created on Jan. 22, 2020 and electronically submitted via EFS-Web herewith the application is incorporated herein by reference in its entirety.

BACKGROUND OF THE INVENTION

1. Field of the Invention

The present invention relates to a composition for muscle enhancement comprising UNE-L domain of leucyl-tRNA synthetase as an active ingredient.

2. Description of the Related Art

Muscle is the most constituent tissue in the human body. A proper amount of muscle is needed to maintain the human body's functional capabilities and to prevent metabolic diseases. The size of muscle is regulated by intracellular signaling processes that induce anabolism or catabolism in muscle. When the signaling reactions that induce the synthesis of muscle proteins occur more than the signaling reactions that induce the degradation of muscle proteins, the synthesis of muscle proteins increase and as a result the number of muscle fiber increases or the size of muscle increases, which is called muscle hypertrophy. Myocyte differentiation and muscle formation are regulated by various muscle regulatory factors such as myoD, myf5, myogenin or mrf4. Among them, myoD initiates the expression of genes specific for muscle differentiation and induces the differentiation of mesenchymal stem cells into myoblasts. Myogenin, which is regulated by myoD, is the most important factor in the binding of myoblasts and is involved in the formation of myotubes. Muscle fibers formed by the process above are bundled to form muscle at last.

On the other hand, when the signaling reactions that induce the degradation of muscle proteins occur more than the signaling reactions that induce the synthesis of muscle proteins, muscle wasting diseases such as muscular atrophy can be developed. Muscle wasting induced by chronic diseases causes the early loss of mobility and increases the risk of disease associated death. Muscle wasting caused by not using muscle is a particularly serious problem in older people, which can increase fracture rate as well as permanent helplessness and premature death. Approximately 24% of aged people at the age between 65 and 70 are experiencing muscular atrophy due to aging, and about 20% of them are experiencing loss of myofunction. As the human body gets aged, the secretion of such hormones involved in anabolism to synthesize protein, for example growth hormones, sex hormones and insulin-like growth factors, is reduced, so that the synthesis of muscle proteins decreases and the level of tumor necrosis factor-alpha (TNF-α), a circulating inflammatory cytokine, increases. TNF-α is fused with damaged muscle fibers or inhibits the differentiation thereof, and accordingly it accelerates catabolism, which is a function to decompose muscle proteins, resulting in the loss of skeletal muscle tissues.

Leucine is one of the three branched-chain amino acids that play the most important role in muscle formation. It is not only a substrate for protein synthesis but also a nutrient to send a signal that regulates protein metabolism. When leucine was orally administered to rats, the rate of skeletal muscle protein increased (Crozier S J et al., J Nutr. 135: 376-382, 2005). On the other hand, when leucine was eliminated, the protein synthesis was suppressed (Stipanuk M H, Nutr Rev. 65:122-129, 2007). Leucine mediated protein synthesis is affected by mTORC1 (mammalian target of rapamycin complex 1) composed of mTOR (mammalian target of rapamycin), raptor, GβL and Rheb. mTORC1 regulates cell growth by integrating extracellular and intracellular signals such as mitogen, cell energy status, oxygen level and amino acid availability, etc. When mTORC1 is activated, ribosomal S6 kinase 1 (S6K1) and eukaryotic initiator 4E-binding protein 1 (4EBP1) which regulate protein synthesis at translation initiation are phosphorylated.

mTOR is a serine/threonine protein kinase that regulates cell growth, cell proliferation, cell mobility, cell survival, autophagy, protein synthesis and translation by stimuli such as growth factor, nutrition and stress. The mechanism of mTOR is also related to metabolic diseases including obesity and diabetes, and aging induced diseases such as neurodegenerative disease and cardiovascular disease, as well as lifespan control.

Leucyl-tRNA synthetase (LRS) is a class I enzyme of aminoacyl-tRNA synthetase (ARS), an enzyme that is essential for protein synthesis and survival and activates amino acids to associate with tRNA. In higher eukaryotic cells, LRS exists as a component of ARS complex comprising 9 different tRNA synthetases and 3 non-enzymatic components. LRS recognizes leucine, which plays the most important role in muscle formation, for protein synthesis and muscle formation. LRS and its product, Ap4A, act as signaling regulators in immune response mediated by gene expression. If LRS is not working properly, diseases such as cancer, diabetes and aging can be caused.

Phospholipase D (PLD) catalyzes hydrolysis of phosphatidylcholine (PC) to produce phosphatidic acid (PA) that binds to the FKBP12-rapamycin binding domain of mTOR. PLD1 and PA not only mediate the activation of mTORC1 by mitogen but also mediate the activation of mTORC1 by Vps34 (vacuolar protein sorting 34) induced by amino acids. Vps34 is the only class III P1-3-kinase in mammals, which produces phosphatidylinositol-3-phosphate (PI(3)P) from phosphatidylinositol and activates PLD1 under amino acid stimulation.

Thus, the present inventors tried to develop a muscle enhancer. In the course of developing a muscle enhancer, the present inventors confirmed that LRS (leucyl-tRNA synthetase) interacted directly with Vps34 as an amino acid sensor to activate Vps34, Vps34-PLD1 was necessary for the activation of LRS of mTORC1, and UNE-L domain of LRS was necessary for the activation of Vps34 and PLD1, which were important in the activation of mTORC1, leading to the completion of the present invention.

SUMMARY OF THE INVENTION

Invention to provide a composition comprising the UNE-L domain of leucyl-tRNA synthetase or a polynucleotide encoding the same for increasing muscle.

It is another object of the present invention to provide a composition comprising the UNE-L domain of leucyl-tRNA synthetase or a polynucleotide encoding the same for the treatment of muscle disease.

To achieve the above objects, the present invention provides a composition comprising the UNE-L domain of leucyl-tRNA synthetase or a polynucleotide encoding the same as an effective ingredient for increasing muscle.

The present invention also provides a method for increasing muscle, which comprises a step of administering a pharmaceutically effective dose of the UNE-L domain of leucyl-tRNA synthetase or a polynucleotide encoding the same to a subject.

The present invention also provides a use of a composition comprising the UNE-L domain of leucyl-tRNA synthetase or a polynucleotide encoding the same for increasing muscle.

The present invention also provides a pharmaceutical composition comprising the UNE-L domain of leucyl-tRNA synthetase or a polynucleotide encoding the same as an effective ingredient for the prevention or treatment of muscle disease.

The present invention also provides a method for preventing or treating muscle disease, which comprises a step of administering a pharmaceutically effective dose of the UNE-L domain of leucyl-tRNA synthetase or a polynucleotide encoding the same to a subject.

The present invention also provides a use of a pharmaceutical composition comprising the UNE-L domain of leucyl-tRNA synthetase or a polynucleotide encoding the same for the prevention or treatment of muscle disease.

In addition, the present invention provides a screening method of a candidate substance for the prevention or treatment of muscle disease.

Advantageous Effect

The UNE-L domain of LRS according to the present invention is a site that regulates Vps34, so that the domain activates mTORC1 involved in protein synthesis and increases myocyte differentiation and muscle fiber regeneration, suggesting that the domain can be effectively used for muscle augmentation.

BRIEF DESCRIPTION OF THE DRAWINGS

FIG. 1a to 1c are a set of diagrams illustrating the regulation of Vps34 and pS6K1 activity by LRS:

FIG. 1a: treatment of leucine (Leu) to HEK293 cells transduced with lentivirus expressing shRNA against LRS (shLRS) or transduced with a control;

FIG. 1b: same as a above except for the presence or absence of amino acid (AA) treatment; and FIG. 1c: quantitative measurement of PI(3)P level in b above.

FIG. 2 is a diagram illustrating the regulation of Vps34 activity by IRS and EPRS.

FIG. 3a to 3c are a set of diagrams confirming whether LRS induces mTOR activation via Vps34:

FIG. 3a: transfection of myc-LRS with shVps34 or a control, amino acid (AA) treatment;

FIG. 3b: amino acid (AA) stimulation according to SAR405 at various concentrations; and FIG. 3c: transfection of myc-LRS according to the presence or absence of SAR405, amino acid (AA) stimulation.

FIG. 4a to 4d are a set of diagrams illustrating the binding location of Vps34 in LRS:

FIG. 4a: results of immunoprecipitation of LRS or Vps34;

FIG. 4b: results of anti-Flag IP and Western blotting of Myc-Vps34 and Flag-LRS wild type (WT) or a fragment thereof;

FIG. 4c: results of IP and Western blotting of Vps34; and

FIG. 4d: results of anti-Flag IP and Western blotting of Myc-Vps34 and Flag-LRS WT or Flag-LRS F50A/Y52A.

FIG. 5a to 5e are a set of diagrams illustrating the active site of Vps34 in LRS:

FIG. 5a: results of Vps34 kinase assay after transfecting HEK293 cells with bicistronic Myc-Vps34/V5-Vps15 and LRS construct;

FIG. 5b: results of PLD assay after transfecting HEK293 cells with HA-PLD1 and LRS constructs;

FIG. 5c: results of Western blotting after transfecting HEK293 cells with HA-S6K1 and LRS constructs;

FIG. 5d: results of Vps34 lipid kinase assay after transfecting HEK293 cells with Myc-Vps34 and WT-LRS or UNE-L deficient mutant of LRS; and FIG. 5e: results of Western blotting after transfecting HEK293 cells with Myc-S6K1 and WT-LRS or UNE-L deficient mutant of LRS.

FIGS. 6a and 6b are a set of diagrams illustrating the interaction of LRS and Vps34 in a non-autophagic complex:

FIG. 6a: results of Vps34 kinase activity measurement according to IP performed with anti-Atg14L (right) or anti-Vps34 (left); and FIG. 6b: results of immunoprecipitation according to Vps34, Beclin 1 or Atg14L antibody.

FIG. 7 is a diagram illustrating the in vitro regulation of Vps34 activity by LRS with or without leucine stimulation.

FIGS. 8a and 8b is a set of diagrams illustrating the regulation of PLD1 activity according to the expression of shLRS:

FIG. 8a: results of PLD activity assay according to amino acid (AA) stimulation; and;

FIG. 8b: results of PLD activity assay according to leucine (Leu) stimulation.

FIG. 9 is a diagram illustrating the regulation of PLD activity by siIRS and siEPRS.

FIGS. 10a and 10b are a set of diagrams illustrating the regulation of translocation of PLD1 and mTOR to lysosomes by LRS:

FIG. 10a: results of HA immunostaining after transfection with HA-PLD1; and

FIG. 10b: results of immunostaining with mTOR;

FIG. 11 is a diagram illustrating the involvement of PLD1 in the regulation of mTORC1 activity by LRS.

FIG. 12a to 12c are a set of diagrams illustrating the role of leucine binding of LRS in Vps34-PLD pathway:

FIG. 12a: results of Western blotting according to amino acid (AA) treatment after transfection with LRS constructs;

FIG. 12b: results of PI(3)P ELISA after the treatment same as a above; and

FIG. 12c: results of PLD activity assay after the treatment same as above.

FIGS. 13a and 13b is a set of diagrams illustrating the increase of PLD1 activity and S6K1 activity by the UNE-L domain of LRS:

FIG. 13a: results of PLD activity assay; and

FIG. 13b: results of S6K1 activity assay.

FIG. 14 is a diagram illustrating the increase of myogenin expression by the UNE-L domain of LRS.

FIG. 15 is a diagram illustrating the increase of differentiation index, fusion index and myotube size of mouse muscle cells by the UNE-L domain of LRS.

FIG. 16 is a diagram illustrating the increase in CSA (cross sectional area) of muscle fiber in mouse regenerated tibialis anterior by the UNE-L domain of LRS.

FIG. 17 is a diagram illustrating the increase of myogenin and MHC expression by the UNE-L domain.

FIG. 18a to 18c are a diagram illustrating the increase in CSA (cross sectional area) of muscle fiber in the UNE-L domain-expressed tibialis anterior during muscle regeneration:

FIG. 18a: results of increase of CSA (cross sectional area) of muscle fiber;

FIG. 18b: results of quantification of CSA of muscle fibers; and

FIG. 18c: results of the mean value of CSA of muscle fibers.

FIG. 19 is a schematic diagram of LRS.

DESCRIPTION OF THE PREFERRED EMBODIMENTS

Hereinafter, the present invention is described in detail.

The present invention provides a composition comprising the UNE-L domain of leucyl-tRNA synthetase or a polynucleotide encoding the same as an effective ingredient for increasing muscle.

The present invention also provides a method for increasing muscle, which comprises a step of administering a pharmaceutically effective dose of the UNE-L domain of leucyl-tRNA synthetase or a polynucleotide encoding the same to a subject.

The present invention also provides a use of a composition comprising the UNE-L domain of leucyl-tRNA synthetase or a polynucleotide encoding the same for increasing muscle.

The said UNE-L domain of leucyl-tRNA synthetase can include a polypeptide composed of any sequence known to those in the art. In an embodiment of the present invention, the UNE-L domain can be a polypeptide composed of the amino acid sequence represented by SEQ. ID. NO: 1.

The polypeptide above includes not only the amino acid sequence of UNE-L domain but also a polypeptide or its fragment having the same amino acid sequence as the amino acid sequence above. The polypeptide having the same amino acid sequence can have at least 80% homology, particularly at least 902, and more particularly at least 95% homology with the polypeptides of the present invention. The polypeptide can be a variant or a fragment of amino acids having a different sequence caused by deletion, insertion, substitution or a combination thereof of amino acid residues within a range that does not affect the function of the protein. Amino acid exchange in proteins or peptides without affecting the overall molecular activity is well informed to those in the art. In some cases, the polypeptide can be modified by phosphorylation, sulfation, acrylation, glycosylation, methylation and farnesylation, etc.

The polynucleotide can include a polynucleotide composed of any sequence known to those in the art. In an embodiment of the present invention, the polynucleotide encoding the UNE-L domain can be a polynucleotide composed of the nucleotide sequence represented by SEQ. ID. NO: 2.

The polynucleotide above includes not only a polynucleotide encoding the amino acid sequence of UNE-L domain but also a polynucleotide or its fragment having the same nucleotide sequence as polynucleotide above. The polynucleotide having the same nucleotide sequence can have at least 80% homology, particularly at least 90%, and more particularly at least 95% homology with the polynucleotide of the present invention. As described above, the polynucleotide of the present invention can include a variant having substitution, deletion or insertion of one or more nucleotides as long as it can encode a protein having the same activity.

In a preferred embodiment of the present invention, it was confirmed that LRS was a upstream regulator of Vps34 activation (see FIG. 1); the activation of Vps34 was not regulated by IRS and EPRS (see FIG. 2), Vp34 was necessary for mTOR activation mediated by LRS caused by amino acid stimulation (see FIG. 3), the binding site of LRS to Vps34 was present in 361-720 amino acids of LRS (see FIG. 4), and in particular, the UNE-L domain of LRS C-terminus was important for Vps34 activation (see FIG. 5).

It was further confirmed that only non-autophagic Vps34 complex was involved in amino acid-induced mTOR signaling, LRS was specifically binding to Vps34 in the non-autophagic complex (see FIG. 6), LRS regulated directly Vps34 activation and leucine played an important role in that regulation (see FIG. 7), LRS was a upstream regulator of PLD1 (see FIG. 8), mTORC1 was present in the downstream of LRS-PLD pathway (see FIG. 11), LRS knockdown suppressed the amino acid induced translocation of PLD1 and mTOR to lysosome (see FIG. 10), and IRS and EPRS were not PLD regulators (see FIG. 9).

It was also confirmed that LRS-leucine binding was necessary for the activation of Vps34-PLD1 pathway, LRS worked as an amino acid sensor (see FIG. 12), and the expression of C-terminal UNE-L domain of LRS was sufficient to activate PLD1 and S6K1 to the similar extent as wild-type LRS (see FIG. 13).

In addition, it was confirmed that the UNE-L domain increased the expression of myogenin, a marker of mouse muscle cell (C2C12) differentiation (see FIG. 14, FIG. 17), increased differentiation index, fusion index and myotube size of mouse muscle cells (see FIG. 15), and increased CSA of muscle fibers in the tibialis anterior of mice muscle-injured with BaCl$_2$ (see FIG. 16, FIG. 18).

The present invention also provides a pharmaceutical composition comprising the UNE-L domain of leucyl-tRNA synthetase or a polynucleotide encoding the same as an effective ingredient for the prevention or treatment of muscle disease.

The present invention also provides a method for preventing or treating muscle disease, which comprises a step of administering a pharmaceutically effective dose of the UNE-L domain of leucyl-tRNA synthetase or a polynucleotide encoding the same to a subject.

The present invention also provides a use of a pharmaceutical composition comprising the UNE-L domain of leucyl-tRNA synthetase or a polynucleotide encoding the same for the prevention or treatment of muscle disease.

The UNE-L domain can have the characteristics as described above. For example, the UNE-L domain can be a polypeptide composed of the amino acid sequence represented by SEQ. ID. NO: 1. The said polynucleotide can have the characteristics as described above. For example, the polynucleotide can be a polynucleotide composed of the nucleotide sequence represented by SEQ. ID. NO: 2. The muscle disease can be a disease caused by the reduction of muscle, which is exemplified by atony, muscular atrophy, muscular dystrophy, muscle degeneration, myasthenia or sarcopenia.

In a preferred embodiment of the present invention, the present inventors confirmed that LRS directly interacted with Vps34 by acting as an amino acid sensor so that it activated Vps34, Vps34-PLD1 was necessary to mediate mTORC1 activation by LRS, and the UNE-L domain of LRS was necessary for the activation of Vps34, PLD1 and S6K1 which played an important role in the activation of mTORC1 (see FIGS. 1-13).

The pharmaceutical composition can include the UNE-L domain of leucyl-tRNA synthetase according to the present invention as an effective ingredient by 10 to 95 weight % for the total weight of the composition. The pharmaceutical composition of the present invention can include, in addition to the effective ingredient above, one or more effective ingredients having the same or similar function to the same.

The composition of the present invention can include carriers, diluents, excipients, or a combination of at least two of those generally used in biological preparations. The pharmaceutically acceptable carrier can be any carrier that is able to deliver the composition of the present invention in the living body without limitation, which is exemplified by the compounds described in Merck Index, 13$^{th}$ ed., Merck & Co. Inc., such as saline, sterilized water, Ringer's solution, buffered saline, dextrose solution, maltodextrin solution, glycerol, ethanol or a mixture comprising one or more of those components. If necessary, a general additive such as antioxidant, buffer, and bacteriostatic agent can be additionally added.

The composition of the present invention can be prepared by using generally used diluents or excipients such as fillers, extenders, binders, wetting agents, disintegrating agents and surfactants.

The composition of the present invention can be formulated as an oral or a parenteral preparation. Solid formulations for oral administration are tablets, pills, powders, granules, capsules and troches. These solid formulations are prepared by mixing the composition with one or more suitable excipients such as starch, calcium carbonate, sucrose, lactose, gelatin, etc. Lubricants such as magnesium stearate and talc can also be added. Liquid formulations are suspensions, solutions, emulsions and syrups, and these formulations can contain excipients such as wetting agents, sweeteners, aromatics and preservatives.

Formulations for parenteral administration can include injections such as sterilized aqueous solutions, water-insoluble excipients, suspensions and emulsions, etc.

Water insoluble excipients and suspensions can contain propylene glycol, polyethylene glycol, vegetable oil like olive oil, injectable ester like ethylolate, etc.

The composition of the present invention can be administered orally or parenterally according to the desired method, and the parenteral administration can be selected from the group consisting of skin external application, intraperitoneal injection, rectal injection, subcutaneous injection, intravenous injection, intramuscular injection and intrathoracic injection.

The composition according to the present invention is administered in a pharmaceutically effective dose. The effective dose can vary depending on the type of disease, the severity, the activity of the drug, the sensitivity to the drug, the time of administration, the route of administration and the rate of release, the duration of treatment, the drug being used concurrently, and the like. The composition of the present invention can be administered alone or in combination with other therapeutic agents. In combination administration, the administration can be sequential or simultaneous.

However, for the desired effect, the amount of the effective ingredient included in the pharmaceutical composition according to the present invention can be 0.001 to 10,000 mg/kg, particularly 0.1 to 5 g/kg. The composition of the present invention can be administered once a day or several times a day.

In addition, the present invention provides a screening method of a candidate substance for the prevention or treatment of muscle disease, which comprises the following steps:

1) treating the UNE-L domain of leucyl-tRNA synthetase C-terminus and a test sample to the cells expressing Vps34;
2) culturing the cells of step 1); and
3) selecting a test sample that increases the activity of phospholipase D1 (PLD1) or S6 kinase 1 (S6K1) in the culture medium of step 2) by comparing the activity of those in the control group untreated with the UNE-L domain.

The UNE-L domain can have the characteristics as described above. For example, the UNE-L domain can be a polypeptide composed of the amino acid sequence represented by SEQ. ID. NO: 1. The said polynucleotide can have the characteristics as described above. For example, the polynucleotide can be a polynucleotide composed of the nucleotide sequence represented by SEQ. ID. NO: 2. The muscle disease can be a disease caused by the reduction of muscle, which is exemplified by atony, muscular atrophy, muscular dystrophy, muscle degeneration, myasthenia or sarcopenia.

The said test sample can be one or more samples selected from the group consisting of peptides, proteins, antibodies, non-peptide materials, synthetic materials, chemical materials, nucleic acids, natural materials, natural compounds, semisynthetic materials, cell extracts, plant extracts, animal tissue extracts and plasma, but not always limited thereto.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Example 1> Confirmation of Regulation of Vps34 by LRS

The regulation of Vps34 by LRS under amino acid simulation was confirmed by the following method.

<1-1> Regulation of Vps34 and mTORC1 Activity by LRS

The following experiment was performed to confirm whether LRS was a regulator of Vps34 activation.

Particularly, HEK293 cells were transducted with lentivirus expressing LRS shRNA (shLRS) or scrambled sequence shRNA (control). The cells were cultured in DMEM supplemented with 10% fetal bovine serum (FBS) in a 37° C., 5% $CO_2$ incubator for 3 days. As for the LRS shRNA, shLRS-1 (TRCN0000290440) or shLRS-2 (TRCN0000290511) was used. As for the scrambled sequence shRNA, the sRNA previously described (Yoon, et al., J Cell Biol., 2011 195(3); 435-447) was used. Lentivirus packaging and transduction were performed according to the methods described in the following paper (Sun, et al., Proc Natl Acad Sci USA., 2008, 105(24); 8286-8291). The simultaneous expression of Vps15 and Vps34 was necessary for the stability and activity of Vps34, so the cells were transfected with bicistronic Myc-Vps34/V5-Vps15 plasmid (Yan, et al., Biochem J., 2009, 417(3); 747-755), followed by culture in the absence of FBS for overnight. On the next day, the cells were cultured in DMEM without leucine or amino acid for 2 hours, followed by stimulating the cells with 0.8 mM leucine or amino acids at the same concentration as DMEM for 30 minutes. The cell lysate was analyzed by Western blotting according to the conventional method. The intensity of the bands obtained by Western blotting was quantified by measuring the X ray film image density using Image J software.

To perform in vitro Vps34 lipid kinase assay, the Vps34 immunocomplex was washed with PBS containing 1% NP-40 three times, with PBS containing 100 mM Tris (pH 7.4) containing 500 mM LiCl three times, and with TNE buffer (10 mM Tris (pH 7.4), 100 mM NaCl and 1 mM EDTA) twice, then 2 mg/ml of P1 and 10 µCi $^{32}$P-γ-ATP (PerkinElmer) were added to TNE buffer. The reaction was terminated by adding 20 µl of 8 N HCl and lipid was extracted with 160 µl of CHCl$_3$:MeOH (1:1). $^{32}$P-PI(3)P was separated on a thin layer chromatography plate (EMD Chemicals Inc.) using CHCl$_3$:MeOH:NH$_4$OH:water (60:47:2:11.3) as a solvent, followed by measuring Vps34 activity by radiograph. The activity of Vps34 was quantified by standardizing the Vps34 amount included in the immune precipitate determined by quantification of Western blotting. To measure the amount of intracellular PI(3)P, ELISA-format assay was performed according to the manufacturer's protocol, leading to quantification of the amount of PI(3)P from nonlinear fitting of the PI(3)P standard. All quantificative data was presented as mean±standard deviation of the values obtained from at least three independent experiments performed separately. Statistical significance was analyzed by student's t-test (*p≤50.05. **p≤0.01).

As a result, as shown in FIG. 1, knock-down of LRS reduced the phosphorylation of S6K1 protein (expression amount of pS6K1) and the activity of Vps34 induced by leucine (FIG. 1A) or total amino acids (FIG. 1B), and the intracellular PI(3)P level was similar to the activity of Vps34 (FIG. 1C). The phosphorylation of S6K1 (pS6K1) was used as a marker of mTORC1 activity. From the above results, it was confirmed that LRS was an upstream regulator of Vps34 and mTOR.

<1-2> Confirmation of Vps34 Activity Regulation by IRS and EPRS

The following experiment was performed to investigate whether the activity of Vps34 was regulated by isoleucyl-tRNA synthetase (IRS) and glutamylprolyl-tRNA synthetase (EPRS).

Particularly, Western blotting and in vitro Vps34 lipid kinase assay were performed by stimulating cells with amino acids by the same manner as described in Example <1-1> except that HEK293 cells were transfected with siEPRS or siIRS. The siEPRS and siIRS used herein were those previously described (Han, et al., Cell., 2012, 149(2); 410-424 and Han, et al., J Biol Chem., 2006, 281(50); 38663-38667). All the quantification data was presented as mean±standard deviation of the values obtained from at least three independent experiments performed separately. Statistical significance was analyzed by student's t-test (*p≤0.05. **p≤0.01).

As a result, as shown in FIG. 2, knock-down of IRS and EPRS did not affect the activity of Vps34 induced by leucine (FIG. 2). From the above result, it was confirmed that the activity of Vps34 was not regulated by IRS and EPRS.

<1-3> Confirmation if LRS Induces mTOR Activation Via Vps34

The following experiment was performed to investigate whether LRS activates mTORC1 through Vps34.

Particularly, Western blotting was performed by stimulating cells with amino acids by the same manner as described in Example <1-1> except that HEK293 cells were transduced with lentivirus expressing shRNA against Vps34 (shVps34) and then co-transfected with Myc-LRS and Myc-S6K1. The shRNA against Vps34 used herein was the one previously described (Yoon, et al., J Cell Biol., 2011 195(3); 435-447).

HEK293 cells were treated with SAR405 (APExBIO, US), a Vps34 specific inhibitor, and then amino acid mediated mTORC1 activation was investigated through S6K1 phosphorylation. First, HEK293 cells were treated with SAR405 at the different concentrations of 0.1, 0.3, 1, 3 and 10 µM, and then 3 µM, the concentration at which S6K1 phosphorylation was completely inhibited, was determined as the treatment concentration of SAR405. Western blotting was performed by stimulating cells with amino acids by the same manner as described in Example <1-1> except that HEK293 cells were treated with SAR405 at the concentration of 3 µM and co-transfected with Myc-LRS and Myc-S6K1. At this time, the cells untreated with SAR405 were used as the control. All the quantification data was presented as mean±standard deviation of the values obtained from at least three independent experiments performed separately. Statistical significance was analyzed by student's t-test (*p≤0.05. **p≤0.01).

As a result, as shown in FIG. 3, when LRS was overexpressed, S6K1 phosphorylation was increased. Such effect of LRS was lost by knock-down of Vps34 (FIG. 3A) SAR405 reduced the S6K1 phosphorylation induced by total amino acids (FIG. 3B) and the S6K1 phosphorylation increased by LRS overexpression (FIG. 3C). From the above result, it was confirmed that Vps34 simulated by amino acids was necessary for LRS mediated S6K1 phosphorylation (mTORC1 activation).

<Example 2> Confirmation of Vps34 Binding Location and Active Site in LRS

The following experiment was performed to confirm the Vps34 binding location and active site in LRS.

<2-1> Confirmation of Vps34 Binding Location in LRS

Immunoprecipitation was performed with Vps34 and LRS in order to investigate whether the physical interaction between LRS and Vps34 and the interaction were affected by the presence or absence of amino acid stimulation.

Particularly, MEF cells stimulated by amino acids by the same manner as described in Example <1-1> were washed with cold PBS. At this time, MEF cells unstimulated with amino acids were used as the control. The cells were lysed in mild lysis buffer (MLB: 10 mM Tris (pH 7.5), 2 mM EDTA, 100 mM NaCl, 13 NP-40, 50 mM NaF, 1 mM Na$_3$VO$_4$ and protease inhibitor cocktail (Sigma)). On the other hand, for immunoprecipitation of LRS, the cells were lysed in MIPT buffer. Then, the lysate was microcentrifuged at 13,000×g for 10 minutes to collect supernatant. An antibody was added to the supernatant at 4° C., followed by immunoprecipitation. Reaction was induced in the presence of protein G-agarose or M2-beads (Sigma). The beads were washed with lysis buffer 3 to 5 times, followed by Western blotting according to the conventional method. Immunoprecipitation for Vps34 was performed with protein G-agarose beads, and immunoprecipitation for Flag-LRS was performed with M2-beads.

To confirm the binding location of LRS to Vps34 and to investigate whether the interaction between LRS and Vps34 was affected by F50A/Y52A mutation, HEK293 cells were transfected with Myc-Vps34, Flag-LRS WT, F50A/Y52A, LRS 1-720 amino acid fragment, LRS 1-976 amino acid fragment, LRS 721-1176 amino acid fragment, LRS 1-360 amino acid fragment or LRS 361-720 amino acid fragment by the same manner as described in Example <1-1>. Plasmids of each amino acid fragment were prepared according to the method described in the following paper (Han, et al., Cell., 2012, 149(2); 410-424) except that cDNA was amplified by PCR and subcloned into pCDNA8-Flag vector. Anti-Flag immunoprecipitation was performed by the same manner as described in Example <2-1>, followed by Western blotting according to the conventional method.

As a result, as shown in FIG. 4, LRS was immunoprecipitated with Vps34, and EPRS, IRS and Vps34 were included in the LRS immunoprecipitate, but only LRS was included in the Vps34 immunoprecipitate (FIG. 4A). In addition, the minimum binding location of LRS to Vps34 was identified in 361-720 amino acids of LRS (FIG. 4B). The interaction between LRS and Vps34 was not affected by the presence or absence of amino acid stimulation (FIG. 4C) or F50A/Y52A mutation (FIG. 4D). Therefore, it was confirmed that the binding location of LRS to Vps34 was present in 361-720 amino acids of LRS (FIG. 19).

<2-2> Confirmation of the Domain of LRS to Activate Vps34

The following experiment was performed to confirm the domain of LRS to activate Vps34 in the course of interaction between LRS and Vps34.

Particularly, in vitro Vps34 lipid kinase assay was performed by stimulating cells with amino acids by the same manner as described in Example <1-1> except that HEK293 cells were transfected with bicistronic Myc-Vps34/V5-Vps15, HA-PLD1 or HA-S6K1 and LRS, LRS 1-720 amino acid fragment or LRS 1-976 amino acid fragment. Western blotting was also performed with the cell lysate. At this time, the cells unstimulated with amino acids were used as the control.

For in vivo PLD assay, HEK293 cells distributed in a 12-well plate were transfected with HA-PLD1 or LRS, LRS 1-720 amino acid fragment or LRS 1-976 amino acid fragment, to which 5 µCi $^3$H-oleic acid (total volume: 500 µl) was added to each well, followed by culture in the absence of FBS. The cells were stimulated with amino acids by the same manner as described in Example <1-1>. At this time, the cells unstimulated with amino acids were used as the control. The cells were treated with 0.3% 1-butanol for 30 minutes during the stimulation with amino acids, then the cells were lysed and lipid was extracted, followed by thin layer chromatography (Sun, et al., Proc Natl Acad Sci USA., 2008, 105(24); 8286-8291). The PLD1 activity was quantified by subtracting the PLD activity of the cells transfected with an empty vector from the PLD activity of the cells transected with PLD1.

In vitro Vps34 lipid kinase assay was performed by stimulating cells with amino acids by the same manner as described in Example <1-1> except that HEK293 cells were transfected with Myc-Vps34 or Myc-Vps34 and wild-type LRS or UNE-L domain deficient LRS in order to investigate the role of the UNE-L domain of LRS. Western blotting was also performed with the cell lysate. At this time, the cells unstimulated with amino acids were used as the control. All the quantification data was presented as mean±standard deviation of the values obtained from at least three independent experiments performed separately. Statistical significance was analyzed by student's t-test (*$p \leq 0.05$. **$p \leq 0.01$).

As a result, as shown in FIG. 5, the LRS fragment containing 1-976 amino acids of N-terminal LRS had the sites capable of binding to Vps34, but was not able to activate Vps34 (FIG. 5A), PLD1 (FIG. 5B) and S6K1 (FIG. 5C). In addition, the UNE-L domain deficient LRS reduced the activity of Vps34 (FIG. 5D) and S6K1 induced by amino acids (FIG. 5E). From the above results, it was confirmed that LRS binding to Vps34 alone was not sufficient to activate Vps34 and the UNE-L domain of LRS C-terminus was important for the activity of Vps34 (FIG. 19).

<Example 3> Confirmation of Interaction Between LRS and Vps34 in Non-Autophagic Complex Vps34 is an important autophagy regulator playing an important role in amino acid signaling. In the condition of amino acid deficiency, a Vps34 complex containing Atg14L is involved in autophagy, whereas Vps34 complexes lacking Atg14L are not involved in autophagy (Yuan, et al., Autophagy., 2013, 9(12); 1983-1995). The following experiment was performed to investigate which Vps34 complex among the autophagic Vps34 complex and the non-autophagic Vps34 complex was involved in LRS binding.

Particularly, in order to investigate which Vps34 complex was involved in the activation of mTOR pathway by amino acid signal, MEF cells were cultured in DMEM supplemented with 10% FBS in a 37° C., 5% $CO_2$ incubator. Then, the cells were cultured in the absence of FBS for overnight. On the next day, the cells were cultured in amino acid-free DMEM for 2 hours, and then stimulated with amino acids at the same concentration as DMEM for 30 minutes. At this time, the cells unstimulated with amino acids were used as the control. Anti-Atg14L antibody was added to the cell lysate, followed by immunoprecipitation to eliminate Atg14L from the cell lysate. Anti-Atg14L or anti-Vps34 antibody was added thereto, followed by immunoprecipitation by the same manner as described in Example <2-1>. Then, in vitro Vps34 lipid kinase assay was performed by the same manner as described in Example <1-1>.

To investigate which Vps34 complex was binding to LRS, Vps34, Beclin1 or Atg14L antibody was added to the cell lysate above, followed by immunoprecipitation by the same manner as described in Example <2-1>. Then, Western blotting was performed.

As a result, as shown in FIG. 6, Vps34 was activated by amino acid stimulation in the absence of Atg14L (left, FIG. 6A). However, in the presence of Atg14L, Vps34 was suppressed by amino acid stimulation (right, FIG. 6A). It was also confirmed that LRS was found in the non-autophagic Vps34 complex separated by immunoprecipitation using Vps34 or Beclin1 antibody in the absence of Atg14L (FIG. 6B). However, it was confirmed that LRS was not present in the autophagic Vps34 complex separated by immunoprecipitation in the presence of Atg14L (FIG. 6B). From the above results, it was confirmed that only non-autophagic Vps34 complex was involved in amino acid induced mTOR signaling, and LRS specifically bound to Vps34 in the non-autophagic complex.

<Example 4> Confirmation of the Regulation of Vps34 Activity by LRS According to Leucine Stimulation The following experiment was performed to investigate the regulation of Vps34 activity by LRS according to the presence or absence of leucine stimulation.

Particularly, MEF cells were cultured in the absence of FBS for overnight. On the next day, the cells were cultured in leucine-free DMEM for 2 hours. Anti-Atg14L antibody was added in the cell lysate thereto, followed by immunoprecipitation to eliminate Atg14L from the cell lysate. Then, anti-Vps34 antibody was added thereto, followed by immunoprecipitation of Vps34. The Vps34 immune complex was placed in TNE buffer supplemented with 2 mg/ml of PI, 10 μCi $^{32}$P-γ-ATP (PerkinElmer) and 3.75 μg of GST protein in the presence or absence of leucine for 20 minutes at 30° C. The GST protein was expressed in *E. coli* BL21 and then purified using glutathione sepharose 4B (GE Healthcare) according to the manufacturer's protocol. Then, Vps34 lipid kinase assay was performed by the same manner as described in Example <1-1>. All the quantification data was presented as mean±standard deviation of the values obtained from at least three independent experiments performed separately. Statistical significance was analyzed by student's t-test (*$p \leq 0.05$. **$p \leq 0.01$).

As a result, as shown in FIG. 7, when the purified GST-LRS protein was added to the Vps34 immune complex, the activity of Vps34 was increased by about 3 times compared to the GST control, and the activity was further increased by leucine stimulation. LRS mutation (F50A/Y52A) did not induce the activation of Vps34, regardless of the presence or absence of leucine stimulation (FIG. 7). From the above results, it was confirmed that LRS directly regulated the activity of Vps34 and thus the regulation of LRS by leucine was very important for the activity of Vps34.

<Example 5> Confirmation of Regulation Between LRS and PLD1

<5-1> Confirmation of PLD1 Activity Regulation by LRS

The following experiment was performed to investigate whether LRS was a regulator of PLD1 activity.

Particularly, in vivo PLD assay was performed by the same manner as described in Example <2-2> by stimulating cells with leucine or amino acids by the same manner as described in Example <1-1> except that HEK293 cells were transduced with shLRS lentivirus or scrambled sequence shRNA (control).

As a result, as shown in FIG. 8, knock-down of LRS suppressed the activity of PLD1 induced by total amino acids (FIG. 8A) or leucine (FIG. 8B). From the above results, it was confirmed that LRS was an upstream regulator of PLD1.

<5-2> Confirmation of the Regulation of PLD Activity by IRS and EPRS

The following experiment was performed to investigate whether the activity of PLD was regulated by isoleucyl-tRNA synthetase (IRS) and glutamylprolyl-tRNA synthetase (EPRS).

Particularly, in vivo PLD assay was performed by the same manner as described in Example <2-2> by stimulating cells with leucine by the same manner as described in Example <1-1> except that HEK293 cells were transfected with siEPRS or siIRS.

As a result, as shown in FIG. 9, knock-down of IRS and EPRS did not affect the activation of PLD induced by leucine (FIG. 9). From the above results, it was confirmed that neither IRS nor EPRS was a regulator of PLD.

<5-3> Confirmation of Translocation of PLD1 and mTOR to Lysosome by LRS

The following experiment was performed to investigate whether LRS was involved in the translocation of PLD1 and mTOR to lysosome according to the amino acid signal.

Particularly, in order to observe immunofluorescence images, HEK293 cells cultured on a glass cover slip coated with poly-L-lysine were transduced with shLRS lentivirus, followed by transfection with HA-PLD1 (Fang, et al., Curr Biol., 2003, 13(23); 2037-2044). Then, the cells were stimulated with amino acids by the same manner as described in Example <1-1>. At this time, the cells untransfected with HA-PLD1 were used as the control. The cells were fixed with 3.7% paraformaldehyde and the permeability thereof was increased with 0.12 Triton X-100. Anti-mTOR (Cell signaling technology), anti-HA (Covance) or anti-LAMP1/2 (Abcam) primary antibody was added to PBS containing 3% BSA, which was reacted with cells for overnight, followed by reaction at room temperature for 30 minutes. Alexa-anti-mouse 594 or Alexa-anti-rabbit 488 antibody was added to PBS containing 3% BSA, which was reacted with cells for 30 minutes at room temperature. Upon completion of the reaction, fluorescence images were analyzed with a personal deconvolution microscope system (DeltaVision, Applied Precision) using 60×NA 1.4 lens. For deconvolution, an improved rate iterative constraint algorithm (Agard et al., 1989) was used. XY and Z optical displacements between different filter sets were determined using Tetraspeck fluorescent microsphere standard (Invitrogen). For quantitative analysis of colocalization, fluorescence images were obtained using a Laser Scanning confocal microscope 700 (LSM 700, Carl Zeiss) equipped with an LSM T-PMT camera (Carl Zeiss, LSM 700). Overlap coefficients were measured using ZEN2009 software. The colocation of each sample was determined as the average of the overlap coefficients for at least 10 cells. All the quantification data was presented as mean±standard deviation of the values obtained from at least three independent experiments performed separately. Statistical significance was analyzed by student's t-test (*$p \leq 0.05$. **$p \leq 0.01$).

As a result, as shown in FIG. 10, knock-down of LRS suppressed the translocation of PLD1 to lysosome induced by amino acids (FIG. 10A), and also inhibited the translocation of mTOR to lysosome (FIG. 10B).

<5-4> Confirmation of PLD1 Involvement in Regulating mTORC1 Activity by LRS

The following experiment was performed to investigate whether PLD1 was involved in the regulation of mTORC1 activity by LRS.

Particularly, HEK293 cells were transduced with shLRS, shRagD lentivirus or lentivirus expressing scrambled sequence shRNA (control), and then stimulated with amino acids by the same manner as described in Example <1-1> in the presence or absence of 100 μM phosphatidic acid (PA), a product of PLD1. Lysates of the cells were analyzed by Western blotting according to the method conventionally performed.

As a result, as shown in FIG. 11, when LRS was knocked-down, the amount of phosphorylated S6K1 was reduced, which was increased again by exogenous PA (FIG. 11). In addition, when both LRS and RagD were all knocked-down, the amount of S6K1 phosphorylated by exogenous PA was partially increased. From the above results, it was confirmed that the regulation of PLD1 by LRS was required in the amino acid induced mTOR signaling along with the regulation of RagD by LRS in RagD-mTORC1 signaling, and PLD1 regulated mTORC1 activity by LRS regardless of LRS-RagD pathway.

<Example 6> Confirmation of Role of Leucine Binding of LRS in Vps34-PLD Pathway

The following experiment was performed to confirm whether the leucine binding of LRS was involved in Vps34-PLD1 signaling regulation.

Particularly, two LRS mutants, which were leucine binding deficient mutant (F50A/Y52A) and tRNA charging-deficient mutant (K716A/K719A), were constructed (Han, et al., Cell., 2012, 149(2); 410-424). Western blotting and PI(3)P assay were performed by the same manner as described in Example <1-1> except that HEK293 cells were transfected with LRS, LRS-F50A/Y52A or LRS-K716A/K719A. And, PLD assay was performed by the same manner as described in Example <2-2> except that HEK293 cells were transfected with HA-PLD1 and LRS, LRS-F50A/Y52A or LRS-K716A/K719A to measure the activity of PLD1. All the quantification data was presented as mean±standard deviation of the values obtained from at least three independent experiments performed separately. Statistical significance was analyzed by student's t-test (*$p \leq 0.05$. **$p \leq 0.01$).

As a result, as shown in FIG. 12, the expression of LRS or LRS-K716A/K719A increased the activity of S6K1 mediated by amino acid stimulation (FIG. 12A). The expression of LRS or K716A/K719A also increased the level of PI(3)P and the activity of PLD1, but F50A/Y52A did not affect thereto (FIGS. 12B and 12C). From the above results, it was confirmed that the leucine binding of LRS was necessary for the activation of Vps34-PLD1 pathway and LRS acted as an amino acid sensor independently of its canonical function in translation regulation (FIG. 19).

<Example 7> Confirmation of Increase of PLD1 Activity and S6K1 Activity by UNE-L Domain of LRS The following experiment was performed to investigate the effect of the UNE-L domain of LRS on the increase of mTOR activity.

Particularly, to investigate the role of the UNE-L domain of LRS, Western blotting was performed with the cell lysate by stimulating cells with amino acids by the same manner as described in Example <1-1> except that HEK293 cells were transfected with LRS UNE-L domain amino acid fragment and wild-type LRS (WT LRS), respectively with myc-S6K1. At this time, to confirm the effect of the UNE-L domain of LRS, wild-type LRS was used as the positive control and the cells unstimulated with amino acids were used as the control.

For in vivo PLD assay, HEK293 cells distributed in a 12-well plate were transfected with HA-PLD1 together with wild-type LRS or LRS UNE-L domain amino acid fragment, to which 5 μCi $^3$H-oleic acid (total volume: 500 μl) was added to each well, followed by serum starvation for one day. The cells were stimulated with amino acids by the same manner as described in Example <1-1>. At this time, in order to confirm the effect of the UNE-L domain of LRS, wild-type LRS was used as the positive control and the cells unstimulated with amino acids were used as the control. The cells were treated with 0.3% 1-butanol for 30 minutes during the stimulation with amino acids, then the cells were lysed and lipids were extracted, followed by thin layer chromatography (Sun, et al., Proc Natl Acad Sci USA., 2008, 105(24); 8286-8291). The PLD1 activity was quantified by subtracting the PLD activity of the cells transfected with an empty vector from the PLD activity of the cells transected with PLD1.

As a result, as shown in FIG. 13, the expression of only UNE-L domain of LRS was able to activate PLD1 (FIG. 13A) and S6K1 (FIG. 13B) to the similar extent as wild-type LRS. From the above results, it was confirmed that the UNE-L domain of LRS C-terminus was an important region to regulate the activity of PLD1 and S6K1.

<Example 8> Confirmation of Effect of LRS UNE-L Domain on Muscle Increasing

<8-1> Confirmation of Enhancement of Differentiation in Mouse Muscle Cell (C2C12) and Increase of S6K1 Activity The following experiment was performed to investigate the effect of the UNE-L domain of LRS on the enhancement of differentiation in mouse muscle cell C2C12.

Particularly, to investigate the role of the UNE-L domain of LRS, NP-UNE-L was constructed by binding the UNE-L domain of LRS to nanoparticles (NP) through the conventional method. The experiment was performed using NP which did not contain UNE-L as the control.

C2C12 cells, the mouse muscle cells, were maintained in DMEM supplemented with 4.5 g/l of glucose and 10% FBS in a 37° C., 7.5% $CO_2$ incubator. To induce myogenesis, the cells were cultured on a plate coated with 0.2% gelatin until 100% confluence and the culture medium was replaced with the differentiation-inducing medium containing 2% horse serum. The culture medium was replaced every day for 3 days. During differentiation for three days, the differentiation-inducing medium treated group, the differentiation-inducing medium and NP-UNE-L treated group, and the differentiation-inducing medium and NP treated group were compared.

After the differentiation of C2C12 cells for three days, Western blotting was performed with the cell lysate according to the conventional method. To compare the differentiation level of C2C12 cells, C2C12 cells were fixed and immunostained with MHC, a myocyte differentiation marker, and 4',6-diamidino-2-phenylindole (DAPI), a cell nucleus marker (Yoon et al. 2013 Molecular biology of the cell, 24(23) 3754-3763). The stained cells were observed with Leica DMI 4000B fluorescence microscope, and fluorescent images were photographed using RETIGA EXi camera. The differentiation index was calculated as the percentage of nuclei in the myotubes stained with MHC and the fusion index was calculated as the percentage of nuclei in the myotubes with two or more nuclei stained with MHC. The myotube size was calculated as the number of nuclei in the myotube stained with MHC.

As a result, as shown in FIG. 14, the phosphorylation of T389 of S6K1, that is the activity of mTORC1, was significantly increased during the differentiation of C2C12 cells by NP-UNE-L. At the same time, the expression of myogenin, the differentiation marker, was also increased in the UNE-L domain treated group.

As shown in FIG. 15, it was confirmed that the differentiation index and the fusion index of C2C12 cells, and the myotube size were all increased, suggesting that UNE-L enhanced the differentiation of muscle cells. The above results indicate that the increased mTOR activity by UNE-L domain results in enhancement of muscle cell differentiation.

<8-2> Confirmation of Increase of Muscle Regeneration in Muscle Injury Induced by $BaCl_2$ The following experiment was performed to investigate the effect of the UNE-L domain of LRS on enhancement of muscle regeneration in muscle injury.

Particularly, $BaCl_2$ (prepared in saline at the concentration of 1.2% wt/vol: 50 μl) was injected into the tibialis anterior (TA) muscles of 10-week-old BL6 mice to induce muscle injury (Sun et al., 2011, J. Cell Biol. 192, 69-81). NP-UNE-L was injected with $BaCl_2$ on the left side and NP was injected with BaCl$_2$ on the right side. 7 days later, the mice were sacrificed and the tibialis anterior muscles were separated and placed in 2-methylbutane which was coldly prepared in liquid nitrogen, followed by embedding in TBS tissue freezing medium. Cryosection was performed at −20° C. to the thickness of 10 μm by using a cryostat (Microm HM550; Thermo Fisher Scientific). The prepared sections were placed on non-coated slides, followed by staining with hematoxylin and eosin (H&E). The stained slides were observed through a 10× dry objective lens of a microscope (DMI 4000B; Leica). The stained images were photographed with a 24-bit image camera (RETIGA EXi; Q Imaging) and the regenarating myofiber cross section area (CSA) was measured by image J. CSA was measured only in the myofibers showing the characteristics of regenerating myofiber with the nucleus in the center.

As a result, as shown in FIG. 16, it was confirmed that CSA of the muscle fibers generated during muscle regeneration was increased in the tibialis anterior (TA) treated with UNE-L, suggesting that the UNE-L domain had an effect on enhancement of muscle regeneration. These results proved that the UNE-L domain had a potential as a muscle enhancer that can promote muscle regeneration.

<Example 9> Confirmation of Effect of LRS UNE-L Domain on Muscle Increasing

<9-1> Confirmation of Enhancement of Myogenesis in Mouse Muscle Cells (C2C12) and Increase of S6K1 Activity The following experiment was performed to investigate the effect of the UNE-L domain LRS on the enhancement of the mouse muscle cell C2C12 differentiation.

Particularly, to investigate the role of the UNE-L domain of LRS, AAV-UNE-L expressing the UNE-L domain of LRS was constructed by using adeno associated virus (AAV) vector. The experiment was performed using the virus that did not contain UNE-L and express GFP as the control.

C2C12 cells, the mouse muscle cells, were maintained in DMEM supplemented with 4.5 g/l of glucose and 10% FBS in a 37° C., 7.5% CO$_2$ incubator. After infecting the cells with AAV-UNE-L or AAV-GFP, the cells were cultured on a plate coated with 0.2% gelatin until 100% confluence to induce muscle cell differentiation, and the culture medium was replaced with the differentiation-inducing medium containing 2% horse serum. The culture medium was replaced every day for 3 days. After the differentiation for two days, the AAV-UNE-L expressing group and the AAV-GFP expressing group were compared.

After the differentiation of C2C12 cells for two days, Western blotting was performed with the cell lysate according to the conventional method.

As a result, as shown in FIG. 17, the phosphorylation of T389 of S6K1, shown the activity of mTORC1, was significantly increased during the differentiation of C2C12 cells by the expression of AAV-UNE-L. At the same time, the expression of myogenin and MHC, the differentiation markers, was also increased in the UNE-L domain expressing group, suggesting that UNE-L enhanced the differentiation of muscle cells. The above results indicate that the increased mTOR activity by UNE-L domain results in the promotion of muscle cell differentiation.

<9-2> Confirmation of Increase of Muscle Regeneration in Muscle Injury Induced by BaCl$_2$ The following experiment was performed to investigate the effect of the UNE-L domain of LRS on the enhancement of muscle regeneration in muscle injury.

Particularly, AAV-UNE-L was injected into the left tibialis anterior (TA) of 10-week-old BL6 mice and AAV-GFP was injected into the right tibialis anterior (TA) of 10-week-old BL6 mice, and after 7 weeks, BaCl$_2$ (prepared in saline at the concentration of 1.2% wt/vol: 50 μl) was injected to induce muscle injury (Sun et al., 2011, J. Cell Biol. 192, 69-81). 7 days later, the mice were sacrificed and the tibialis anterior muscles were separated and fixed in 10% paraformaldehyde, followed by embedding in paraffin. The section was performed to the thickness of 10 μm, and the prepared sections were placed on non-coated slides, followed by staining with hematoxylin and eosin (H&E). The stained slides were observed through a 10× dry objective lens of a microscope (Olympus CKX3-Houn Microscope). The stained images were photographed with 24-bit image and the regenarating myofiber cross section area (CSA) was measured by image J. CSA was measured only in the myofibers showing the characteristics of regenerating myofiber with the nucleus in the center.

As a result, as shown in FIG. 18, CSA of the muscle fibers generated during muscle regeneration was increased in the muscles expressing UNE-L (FIGS. 18A and 18B), and the mean value of CSA was increased significantly in the tibialis anterior (TA) expressing UNE-L (FIG. 18C), suggesting that the UNE-L domain had an effect on promoting muscle regeneration. These results proved that the UNE-L domain had a potential as a muscle enhancer that can promote muscle regeneration.

What is claimed is:

1. A method for increasing muscle, comprising administering a pharmaceutically effective dose of the UNE-L domain amino acid sequence of leucyl-tRNA synthetase (LRS) according to SEQ. ID. NO:1 or a polynucleotide encoding the same to a subject.

2. The method for increasing muscle according to claim 1, wherein the polynucleotide is a polynucleotide comprising the nucleotide sequence represented by SEQ. ID. NO: 2.

3. The method for increasing muscle according to claim 1, wherein administering the UNE-L domain activates Vps34 (vacuolar protein sorting 34).

4. A method for preventing or treating muscle disease, comprising administering a pharmaceutically effective dose of the UNE-L domain amino acid sequence of leucyl-tRNA synthetase (LRS) according to SEQ. ID. NO:1 or a polynucleotide encoding the same to a subject.

5. The method for the prevention or treatment of muscle disease according to claim 4, wherein the muscle disease is atony, muscular atrophy, muscular dystrophy, muscle degeneration, myasthenia or sarcopenia.

6. A screening method of a candidate substance for the prevention or treatment of muscle disease, comprising the following steps:
1) applying the UNE-L domain of leucyl-tRNA synthetase C-terminus (SEQ: ID: 1) and a test sample to cells expressing Vps34 (vacuolar protein sorting 34) protein;
2) culturing the cells of step 1); and
3) selecting a test sample that increases the activity of phospholipase D1 (PLD1) or S6 kinase 1 (S6K1) in the culture medium of step 2) by comparing the activity of those in the control group not-treated with the UNE-L domain.

* * * * *